(12) United States Patent
Winn et al.

(10) Patent No.: US 11,209,442 B2
(45) Date of Patent: Dec. 28, 2021

(54) IMAGE SELECTION SUGGESTIONS

(71) Applicant: Google LLC, Mountain View, CA (US)

(72) Inventors: Julia Winn, Mountain View, CA (US); Timothy Novikoff, Mountain View, CA (US); Juan Carlos Anorga, San Francisco, CA (US)

(73) Assignee: Google LLC, Mountain View, CA (US)

( * ) Notice: Subject to any disclaimer, the term of this patent is extended or adjusted under 35 U.S.C. 154(b) by 0 days.

(21) Appl. No.: 16/619,410

(22) PCT Filed: Dec. 21, 2018

(86) PCT No.: PCT/US2018/067242
§ 371 (c)(1),
(2) Date: Dec. 4, 2019

(87) PCT Pub. No.: WO2019/126723
PCT Pub. Date: Jun. 27, 2019

(65) Prior Publication Data
US 2020/0150832 A1    May 14, 2020

Related U.S. Application Data

(60) Provisional application No. 62/609,543, filed on Dec. 22, 2017.

(51) Int. Cl.
*G06F 3/0482* (2013.01)
*G06F 16/54* (2019.01)
(Continued)

(52) U.S. Cl.
CPC ....... *G01N 33/6884* (2013.01); *A61K 31/522* (2013.01); *A61K 31/573* (2013.01);
(Continued)

(58) Field of Classification Search
CPC .............................. G06F 16/54; G06F 3/0482
See application file for complete search history.

(56) References Cited

U.S. PATENT DOCUMENTS 8,589,402 B1 * 11/2013 Iampietro ........... G06F 16/5866
707/741
8,909,625 B1 * 12/2014 Stewenius ............... G06F 16/54
707/723

(Continued)

FOREIGN PATENT DOCUMENTS

JP      H0973530        3/1997
JP      2003-248699     9/2003

(Continued)

OTHER PUBLICATIONS

WIPO, International Preliminary Report on Patentability mailed for International application No. PCT/US2018/067242, dated Jan. 16, 2020, 21 pages.

(Continued)

*Primary Examiner* — Jennifer N Welch
*Assistant Examiner* — Reji Kartholy
(74) *Attorney, Agent, or Firm* — IP Spring

(57) ABSTRACT

Implementations are related to providing image selection suggestions. In some implementations, a method includes receiving first user input indicative of selection of one or more first images in an image library and determining one or more first image characteristics of the one or more first images. The method further includes identifying one or more second images in the image library. Each image of the one or more second images is associated with at least one second image characteristic that matches at least one of the one or more first image characteristics. The method further includes causing a user interface to be displayed. The user interface includes the one or more second images and (Continued)

enables selection of the one or more second images by a user.

18 Claims, 8 Drawing Sheets

(51) Int. Cl.
| | |
|---|---|
| *G01N 33/68* | (2006.01) |
| *C07K 16/28* | (2006.01) |
| *C07K 16/24* | (2006.01) |
| *A61K 39/395* | (2006.01) |
| *C07K 16/18* | (2006.01) |
| *A61K 31/522* | (2006.01) |
| *A61K 31/573* | (2006.01) |
| *A61K 45/06* | (2006.01) |

(52) U.S. Cl.
CPC .... *A61K 39/3955* (2013.01); *A61K 39/39566* (2013.01); *A61K 45/06* (2013.01); *C07K 16/18* (2013.01); *C07K 16/244* (2013.01); *C07K 16/28* (2013.01); *G01N 33/6887* (2013.01); *G01N 33/6893* (2013.01); *G01N 2333/475* (2013.01); *G01N 2800/122* (2013.01); *G01N 2800/52* (2013.01)

(56) References Cited

U.S. PATENT DOCUMENTS

| | | | |
|---|---|---|---|
| 9,715,731 | B2 | 7/2017 | Desnoyer et al. |
| 10,038,656 | B2 | 7/2018 | Zheng et al. |
| 2007/0220045 | A1 | 9/2007 | Morris et al. |
| 2011/0026835 | A1* | 2/2011 | Ptucha .................. G06F 16/583 382/209 |
| 2012/0020576 | A1* | 1/2012 | Fry ....................... G06F 3/0482 382/218 |
| 2013/0125069 | A1 | 5/2013 | Bourdev et al. |
| 2014/0244514 | A1* | 8/2014 | Rodriguez ......... G06Q 20/3223 705/71 |
| 2014/0372951 | A1 | 12/2014 | Li et al. |
| 2015/0149454 | A1* | 5/2015 | Hieronymus ......... G06F 16/583 707/728 |
| 2015/0227797 | A1 | 8/2015 | Ko et al. |
| 2015/0301695 | A1* | 10/2015 | Leong .................. G06F 16/5866 715/838 |
| 2015/0371366 | A1* | 12/2015 | Hilt ....................... G06T 3/4038 382/284 |
| 2016/0042253 | A1* | 2/2016 | Sawhney ............. G06K 9/6218 382/190 |
| 2016/0321783 | A1* | 11/2016 | Citrin ................. H04N 1/32106 |
| 2017/0249339 | A1* | 8/2017 | Lester ..................... G06F 16/56 |
| 2018/0083898 | A1 | 3/2018 | Pham |
| 2018/0150433 | A1 | 5/2018 | Sowden et al. |
| 2018/0164990 | A1* | 6/2018 | Lin ....................... G11B 27/34 |
| 2018/0336226 | A1 | 11/2018 | Anorga et al. |
| 2018/0336415 | A1 | 11/2018 | Anorga et al. |
| 2019/0121879 | A1* | 4/2019 | Canelis ............... G06F 3/04845 |
| 2019/0197364 | A1 | 6/2019 | Cheng et al. |

FOREIGN PATENT DOCUMENTS

| | | |
|---|---|---|
| JP | 2007-188404 | 7/2007 |
| JP | 2010-146201 | 7/2010 |
| JP | 2012-079337 | 4/2012 |
| JP | 2012-133507 | 7/2012 |
| JP | 2015-069277 | 4/2015 |
| WO | WO2017197826 | 11/2017 |

OTHER PUBLICATIONS

"Resizing Large Images Using IRFANVIEW", URL:http://web.archive.org/web/20030811010516/http://www.somewhere-in-time.net/tutorial/irfanview, Aug. 11, 2003, pp. 1-6.

IPO, First Examination Report for Indian Patent Application No. 202047021751, dated Jun. 28, 2021, 7 pages.

JPO, Office Action for Japanese Patent Application No. 2020-528152, dated Jun. 15, 2021, 9 pages.

Kamioka, et al., "Decision support system using content-based image retrieval interface", Journal of Human Interface Society, vol. 5, No. 3, Aug. 26, 2003, 9 pages.

EPO, Communication Pursuant to Article 94(3) EPC for European Patent Application No. 18837058.9, dated Aug. 16, 2021, 8 pages.

* cited by examiner

IMAGE SELECTION SUGGESTIONS

CROSS-REFERENCE TO RELATED APPLICATIONS

This application claims priority to U.S. Provisional Patent Application No. 62/609,543, filed Dec. 22, 2017, entitled, "Image Selection Suggestions," and which is incorporated by reference herein in its entirety.

BACKGROUND

The popularity and convenience of digital camera devices have caused visual content such as digital photographs and videos to become ubiquitous. For example, large numbers of images of various types can be captured, stored, and displayed by user devices. Some devices allow a user's images or other content to be displayed in a layout including content items in a collection. Typically, a view of content items is displayed on a screen, and the user may cause the content items to scroll such that different portions of the collection of content items are displayed in the view. The user may also select one or more content items for various purposes such as sharing with other users, generating a picture collage, a photo book, etc.

The background description provided herein is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

SUMMARY

Implementations of this application relate to image selection suggestions. In some implementations, a computer-implemented method includes receiving first user input indicative of selection of one or more first images in an image library; determining one or more first image characteristics of the one or more first images; identifying one or more second images in the image library, where each of the one or more second images is associated with at least one second image characteristic that matches at least one of the one or more first image characteristics; and causing a user interface to be displayed, where the user interface includes the one or more second images, and where the user interface enables selection of the one or more second images.

These and other implementations may each optionally include one or more of the following features: receiving second user input indicative of selection of at least one of the one or more second images; in response to receiving the second user input, determining one or more second image characteristics of the at least one of the one or more second images; identifying one or more third images in the image library, where each of the one or more third images is associated with at least one third image characteristic that matches least one of the one or more first image characteristics and at least one of the one or more second image characteristics; and causing an updated user interface to be displayed, where the updated user interface includes the one or more third images and where the updated user interface enables selection of the one or more third images.

These and other implementations may each optionally include one or more of the following features: generating an image album, where the image album includes the one or more first images and the at least one of the one or more second images; receiving second user input indicative of selection of at least one of the one or more second images, and generating an image collage, where the image collage includes the one or more first images and the at least one of the one or more second images; determining the one or more first image characteristics comprises determining that the image is blurry, and where identifying the one or more second images includes identifying each of the one or more second images based on blurriness of the one or more second images.

These and other implementations may each optionally include one or more of the following features: determining the one or more first image characteristics comprises determining a location associated with the first image, and identifying the one or more second images comprises selecting images from the image library that are associated with a respective location that is within a threshold distance of the location associated with the first image; the method further comprising determining a context of image selection, where identifying the one or more second images is based on the context of image selection. The context of image selection can be generation of an image-based creation, and/or providing images to a target software application. The image-based creation can comprise at least one of an image album, an image collage, a video, or a printed publication, or a combination of any of these.

These and other implementations may each optionally include one or more of the following features: receiving second user input indicative of selection of at least one of the one or more second images that are duplicates of the first image and based on the one or more first images and the at least one of the one or more second images, causing a suggested action element to be displayed in the user interface. The method can further comprise receiving user selection of the suggested action element; and in response to receiving the user selection, performing an action associated with the suggested action element, where the action includes one or more of: archiving the one or more first images and the at least one of the one or more second images, deleting the one or more first images and the at least one of the one or more second images, and/or performing an automatic enhancement of the one or more first images and the at least one of the one or more second images.

In some implementations, a computer-implemented method determining context information indicative of a target software application; based at least in part on the context information, identifying one or more first images in an image library; causing a user interface to be displayed, where the user interface includes the one or more first images, and the user interface enables selection of the one or more first images; receiving first user input indicative of selection of at least one image of the one or more first images; and in response to receiving the first user input, providing the selected at least one image to the target software application.

These and other implementations may each optionally include one or more of the following features: determining one or more first image characteristics of the selected at least one image; identifying one or more second images in the image library, where each of the one or more second images has at least one of the one or more first image characteristics; and causing an updated user interface to be displayed, where the updated user interface includes the one or more second images, and the user interface enables selection of the one or more second images.

These and other implementations may each optionally include one or more of the following features: determining the context information includes determining an application type of the target software application. The application type can include an image sharing application. Identifying the one or more first images can comprise selecting the one or more first images from the image library that meet a quality threshold. The application type can include a financial application and identifying the one or more first images can comprise selecting the one or more first images from the image library that are associated with an image label that includes one or more of receipt, document, or screenshot. The application type can include a messaging application and determining the context information can further include receiving identification information of participants in a messaging conversation in the messaging application; identifying the one or more first images can comprise selecting images from the image library that depict at least one of the participants in the messaging conversation.

These and other implementations may each optionally include one or more of the following features: determining the context information receiving an application context from the target software application, and where identifying the one or more first images comprises: determining one or more semantic concepts based on the application context; and selecting the one or more first images, where at least one image characteristic of each of the selected images matches at least one of the semantic concepts.

In some implementations, a non-transitory computer-readable medium has instructions stored thereon that, when executed by one or more hardware processors, causes the one or more hardware processors to perform operations comprising receiving first user input indicative of selection of one or more first images in an image library; determining one or more first image characteristics of the one or more first images; identifying one or more second images in the image library, where each of the one or more second images is associated with at least one second image characteristic that matches at least one of the one or more first image characteristics; causing a user interface to be displayed, where the user interface includes the one or more second images, and where the user interface enables selection of the one or more second images; receiving second user input indicative of selection of at least one of the one or more second images; based on the one or more first images and the at least one of the one or more second images, causing a suggested action element to be displayed in the user interface; and in response to receiving user selection of the suggested action element, performing an action associated with the suggested action element. In some implementations, the action includes one or more of: archiving the one or more first images and the at least one of the one or more second images, deleting the one or more first images and the at least one of the one or more second images, generating an image-based creation that includes the one or more first images and the at least one of the one or more second images, or performing an automatic enhancement of the one or more first images and the at least one of the one or more second images.

DETAILED DESCRIPTION

Figure 1:
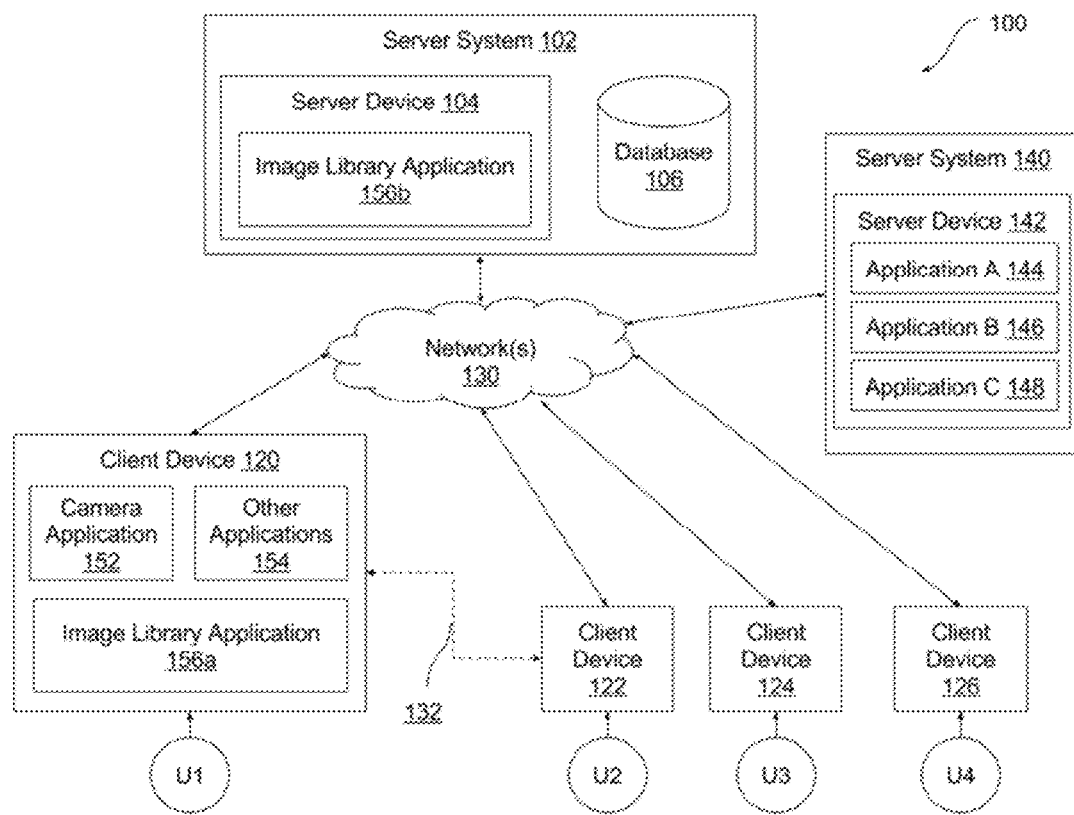
FIG. 1 is a block diagram of an example network environment which may be used for one or more implementations described herein.

One or more implementations aid users to select images. One or more implementations described herein include providing suggested images for a user to select. The implementations provide benefits by providing a user interface that enables users to select images with reduced input such as searching for images using keywords or phrases, browsing an image library by scrolling, etc. The implementations can reduce the computing resources used to support user searching or browsing by providing a user interface that enables users to select images without such activity.

Users select images, e.g., from an image library for a variety of purposes, e.g., to share images with other users, to generate image-based creations such as image albums, image collages, printed photo books, or videos that include images. Users may have image libraries that include a large number of images, e.g., hundreds, thousands, or even millions of images. Finding and selecting images may be difficult for users. For example, when images in an image library are organized and displayed in a chronological manner, users may have to perform multiple scroll operations to view and select images for a particular purpose. Scrolling back and forth to find images of interest is cumbersome and users may find such scrolling frustrating. Further, such user activity of scrolling images requires a computing device to retrieve additional images from memory or storage and to refresh the user interface to show different images, requiring use of computing resources of the computing device.

Image library applications may include image search features. For example, a user may be able to specify a text query and the image library application may return images from the library that are relevant to the search, and the user can select images from the returned images. However, this requires the user to define a query. Further, the user may have to specify multiple different queries to obtain the entire set of images to select. Searching and selecting images via queries is cumbersome. Further, user search activity requires a computing device to access an image library, e.g., stored locally on the computing device or stored on a remote server via network, and identify images that match the user-specified search query, requiring use of computing resources of the computing device.

The implementations described in this document address some of the problems in finding and selecting images from an image library that includes a large number of images. In some implementations, first user input indicative of selection of one or more first images in an image library is received. One or more first image characteristics of the one or more first images are determined. One or more second images in the image library are automatically identified that are each associated with at least one second image characteristic that matches at least one of the one or more first image characteristics. A user interface is displayed that includes the one or more second images, and that enables selection of the one or more second images.

By automatically identifying and presenting images that match user selections, the implementations described herein eliminate the need to display images as the user scrolls through an image library or to display resulting images that satisfy textual search queries specified by user input. As user input selects images, additional images from the user's image library that have matching characteristics are automatically identified and presented for the user to select. In this manner, the techniques described herein present a user interface that enables efficient retrieval from storage, display, and selection of images, enabling easy finding and selection of images. Reduced consumption of device resources is enabled by reducing or avoiding lengthy displays of scrolled images and reducing or avoiding multiple retrievals and displays of search results from text search queries.

The described suggested image selections can enable faster and more efficient display of images in a user interface, and more efficient interaction of a user with the user interface to locate and select images. For example, display of suggested image selections enables a user to easily select images and reduces or eliminates the need to manually provide text or other complex input to specify search queries to determine images to select. Furthermore, the suggested image selections reduce the time and processing for the display of images and reduce the number of manually-specified searches received to find images. Suggested image selections are also useful when a client device lacks easy, simple, or any text input functionality for searches (e.g., a smartwatch or other wearable device that does not include a keyboard or microphone). Such features allow interaction with a content display program with reduced user input and reduced time, thus reducing consumption of device resources that would otherwise be needed to receive and process user input and display results in such programs.

Consequently, a technical effect of one or more described implementations is that display of content data items in user interfaces is provided with less computational time and fewer computational resources expended to obtain results. For example, a technical effect of described techniques and features is a reduction in the consumption of system processing resources utilized to display and select particular images as compared to a prior system that does not provide one or more of the described techniques or features. For example, a prior system may use prior techniques of receiving search queries as text, in which additional computational resources, such as processor, memory and display resources (with corresponding power consumption) are needed to display iterations of search results as the user determines which search queries are relevant to provide images to select.

A further technical effect of described techniques and features is a reduction in the consumption of system processing resources, such as display and search processing and power consumption, utilized by a system that does not provide one or more of the described techniques or features. For example, in such a prior system, the user manually scrolls a view of content elements, and the user must manually locate desired content items via such manual scrolling, leading to inefficient use of system resources (e.g., for repeated display and scrolling of content data items in forward and back directions, repeated reception of commands from users to display and/or search for content items, etc.).

In situations in which certain implementations discussed herein may collect or use personal information about users (e.g., user data, information about a user's social network, user's location and time at the location, user's biometric information, user's activities and demographic information), users are provided with one or more opportunities to control whether information is collected, whether the personal information is stored, whether the personal information is used, and how the information is collected about the user, stored and used. That is, the systems and methods discussed herein collect, store and/or use user personal information specifically upon receiving explicit authorization from the relevant users to do so. For example, a user is provided with control over whether programs or features collect user information about that particular user or other users relevant to the program or feature. Each user for which personal information is to be collected is presented with one or more options to allow control over the information collection relevant to that user, to provide permission or authorization as to whether the information is collected and as to which portions of the information are to be collected. For example, users can be provided with one or more such control options over a communication network. In addition, certain data may be treated in one or more ways before it is stored or used so that personally identifiable information is removed. As one example, a user's identity may be treated so that no personally identifiable information can be determined. As another example, a user device's geographic location may be generalized to a larger region so that the user's particular location cannot be determined.

An image, as referred to herein, is a digital image having pixels with one or more pixel values (e.g., color values, brightness values, etc.). An image can be a still image or single image or can be an image included in a series of images, e.g., a frame in a video sequence of video frames, or an image in a different type of sequence or animation of images. A video includes a sequence of multiple images. For example, implementations described herein can be used with content data items that are single images or static images (e.g., a photograph, an emoji, or other image), videos, or animated images (e.g., cinemagraphs or other animated image that includes motion, a sticker that includes animation and audio, etc.). Text, as referred to herein, can include alphanumeric characters, emojis, symbols, or other characters. An audio segment can include audio data that is provided in a standard audio format which can be processed to provide sound, e.g., from speakers.

FIG. 1 illustrates a block diagram of an example network environment 100, which may be used in some implementations described herein. In some implementations, network environment 100 includes one or more server systems, e.g., server system 102 and second server system 140 in the example of FIG. 1. Server systems 102 and 140 can communicate with a network 130, for example. Server system 102 can include a server device 104 and a database 106 or other storage device. In some implementations, server device 104 may provide an image library application 156b. Second server system 140 can include a second server device 142, configured to provide one or more applications, e.g., a messaging application A 144, an image sharing application B 146, and a financial application C 148.

Network environment 100 also can include one or more client devices, e.g., client devices 120, 122, 124, and 126, which may communicate with each other and/or with server system 102 and/or second server system 140 via network 130. Network 130 can be any type of communication network, including one or more of the Internet, local area networks (LAN), wireless networks, switch or hub connections, etc. In some implementations, network 130 can include peer-to-peer communication between devices, e.g., using peer-to-peer wireless protocols (e.g., Bluetooth®, Wi-Fi Direct, etc.), etc. One example of peer-to-peer communications between two client devices 120 and 122 is shown by arrow 132.

For ease of illustration, FIG. 1 shows one block for server system 102, server device 104, database 106, second server system 140, and second server device 142, and shows four blocks for client devices 120, 122, 124, and 126. Server blocks 102, 104, 106, 140, and 142 may represent multiple systems, server devices, and network databases, and the blocks can be provided in different configurations than shown. For example, server system 102 and/or second server system 140 can represent multiple server systems that can communicate with other server systems via the network 130.

In some implementations, server system 102 and/or second server system 140 can include cloud hosting servers, for example. In some examples, database 106 and/or other storage devices can be provided in server system block(s) that are separate from server device 104 and can communicate with server device 104 and other server systems via network 130. Also, there may be any number of client devices. Each client device can be any type of electronic device, e.g., desktop computer, laptop computer, portable or mobile device, cell phone, smart phone, tablet computer, television, TV set top box or entertainment device, wearable devices (e.g., display glasses or goggles, wristwatch, headset, armband, jewelry, etc.), personal digital assistant (PDA), media player, game device, etc. Some client devices may also have a local database similar to database 106 or other storage. In some implementations, network environment 100 may not have all of the components shown and/or may have other elements including other types of elements instead of, or in addition to, those described herein.

In various implementations, end-users U1, U2, U3, and U4 may communicate with server system 102 and/or each other using respective client devices 120, 122, 124, and 126. In some examples, users U1, U2, U3, and U4 may interact with each other via applications running on respective client devices and/or server system 102 or second server system 140, and/or via a network service, e.g., a social network service or other type of network service, implemented on server system 102 or second server system 140. For example, respective client devices 120, 122, 124, and 126 may communicate data to and from one or more server systems (e.g., system 102, second server system 140).

In some implementations, the server system 102 and/or second server system 140 may provide appropriate data to the client devices such that each client device can receive communicated content or shared content uploaded to the server system 102 or second server system 140 and/or network service. In some examples, users U1-U4 can interact via audio or video conferencing, audio, video, or text chat, or other communication modes or applications. A network service implemented by server system 102 or second server system 140 can include a system allowing users to perform a variety of communications, form links and associations, upload and post shared content such as images, text, video, audio, and other types of content, and/or perform other functions. For example, a client device can display received data such as content posts sent or streamed to the client device and originating from a different client device via a server and/or network service (or from the different client device directly) or originating from a server system and/or network service. In some implementations, client devices can communicate directly with each other, e.g., using peer-to-peer communications between client devices as described above. In some implementations, a "user" can include one or more programs or virtual entities, as well as persons that interface with the system or network.

In some implementations, any of client devices 120, 122, 124, and/or 126 can provide one or more applications. For example, as shown in FIG. 1, client device 120 may provide a camera application 152, an image library application 156a, and one or more other applications 154. Client devices 122-126 may also provide similar applications. For example, camera application 152 may provide a user of a respective client device (e.g., users U1-U4 with the ability to capture images, e.g., using a camera of the respective client device. For example, camera application 152 may be a software application that executes on client device 120. In some implementations, camera application 152 may provide a user interface.

In some implementations, client device 120 may include image library application 156a. Image library application 156a may be implemented using hardware and/or software of client device 120, as described with reference to FIG. 6. In different implementations, image library application 156a may be a standalone image library application, e.g., executed on any of client devices 120-124, or may work in conjunction with image library application 156b provided on server system 102. Image library application 156a and image library application 156b may provide image management functions. Image management functions may include storing photos and videos captured using camera application 152, storing other images, e.g., scanned images, screenshots, etc., image editing functions, functions to generate image-based creations such as an image collage, a video, an image album, or a printed publication (e.g., photo book). Image library application 156 may also programmatically analyze images, e.g., image pixels and image metadata, to determine one or more image characteristics. Image library application 156 may store image data and characteristics, e.g., in local storage of a client device, and/or remote storage of one or more other devices communicating over network 130, e.g., database 106 of server system 102 and/or 140, storage of one or more different client devices, etc.

In some implementations, client device 120 may include one or more other applications 154. For example, other applications 154 may be applications that provide various types of functionality, e.g., calendar, address book, e-mail, web browser, shopping, transportation (e.g., taxi, train, airline reservations, etc.), entertainment (e.g., a music player, a video player, a gaming application, etc.), social networking (e.g., messaging or chat, audio/video calling, sharing images/video, etc.) and so on. In some implementations, one or more of other applications 154 may be standalone applications that execute on client device 120. In some implementations, one or more of other applications 154 may access a server system, e.g., second server system 140, that provides data and/or functionality of applications 154. For example, any of applications 144, 146, and 148, shown as being provided by second server system 140 may provide data and/or commands to one or more of other applications 154. In some implementations, server applications 144-148 may be standalone applications that are accessed by a client device, e.g., via a web-browser, or other client-side program.

A user interface on a client device 120, 122, 124, and/or 126 can enable display of user content and other content, including images, video, data, and other content as well as communications, privacy settings, notifications, and other data. Such a user interface can be displayed using software on the client device, software on the server device, and/or a combination of client software and server software executing on server device 104 and/or second server device 142, e.g., application software or client software in communication with server system 102 and/or second server device 142. The user interface can be displayed by a display device of a client device or server device, e.g., a touchscreen or other display screen, projector, etc. In some implementations, application programs running on a server system can communicate with a client device to receive user input at the client device and to output data such as visual data, audio data, etc. at the client device.

In some implementations, any of server system 102, second server system 140, and/or one or more client devices 120-126 can provide a communication application program. The communication program may allow a system (e.g., client device or server system) to provide options for communicating with other devices. The communication program can provide one or more associated user interfaces that are displayed on a display device associated with the server system or client device. The user interface may provide various options to a user to select communication modes, users or devices with which to communicate, etc. The communication program can display or otherwise output transmitted content posts and received content posts, e.g., in any of a variety of formats.

Other implementations of features described herein can use any type of system and/or service. For example, other networked services (e.g., connected to the Internet) can be used instead of or in addition to a social networking service. Any type of electronic device can make use of features described herein. Some implementations can provide one or more features described herein on one or more client or server devices disconnected from or intermittently connected to computer networks. In some examples, a client device including or connected to a display device can display images stored on storage devices local to the client device, e.g., received previously over communication networks.

Figure 2:
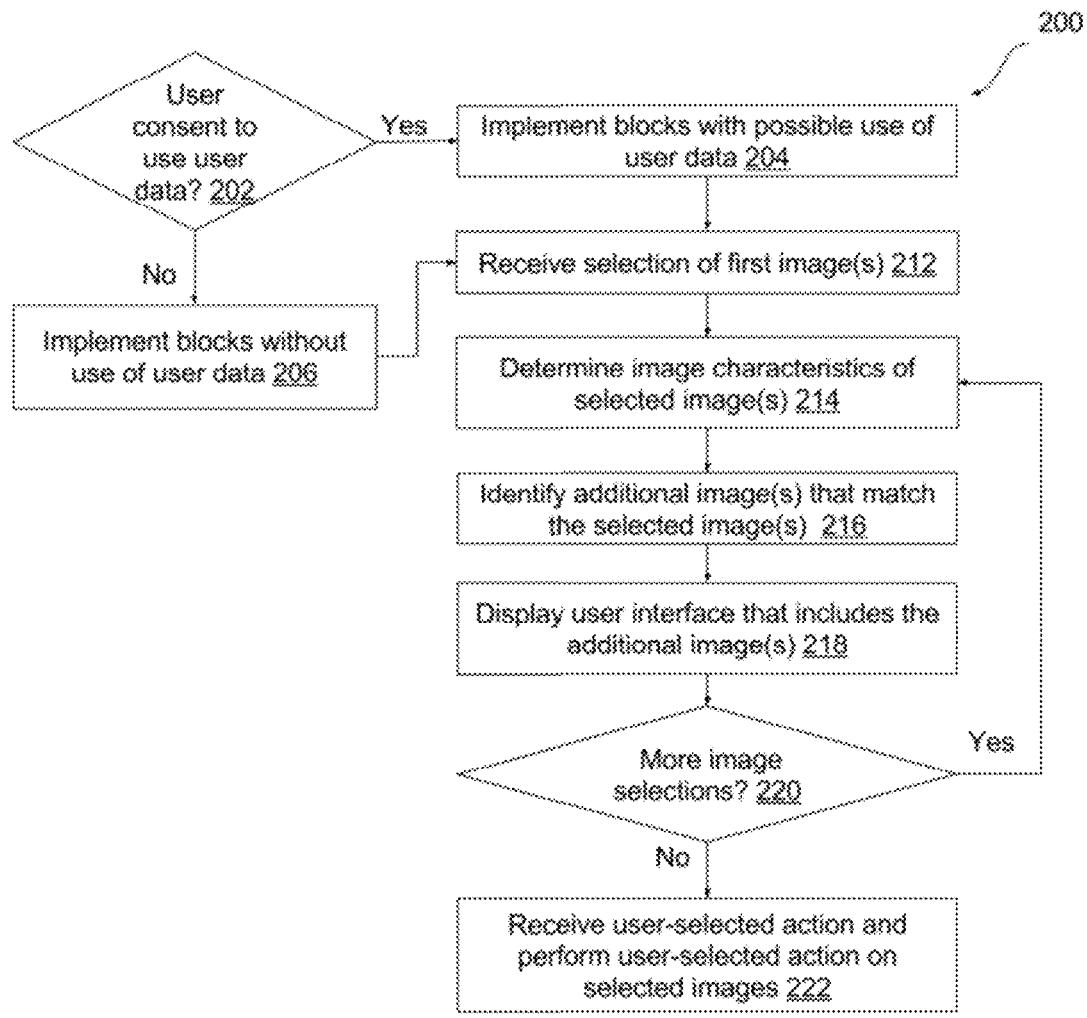
FIG. 2 is a flow diagram illustrating an example method to provide image selection suggestions, according to some implementations.

FIG. 2 is a flow diagram illustrating an example method to provide image selection suggestions, according to some implementations. In some implementations, method 200 can be implemented, for example, on a server system 102 as shown in FIG. 1. In some implementations, some or all of the method 200 can be implemented on one or more client devices 120, 122, 124, or 126 as shown in FIG. 1, one or more server devices, and/or on both server device(s) and client device(s). In described examples, the implementing system includes one or more digital processors or processing circuitry ("processors"), and one or more storage devices (e.g., a database 106 or other storage). In some implementations, different components of one or more servers and/or clients can perform different blocks or other parts of the method 200. In some examples, a first device is described as performing blocks of method 200. Some implementations can have one or more blocks of method 200 performed by one or more other devices (e.g., other client devices or server devices) that can send results or data to the first device.

In some implementations, the method 200, or portions of the method, can be initiated automatically by a system. In some implementations, the implementing system is a first device. For example, the method (or portions thereof) can be periodically performed, or performed based on one or more particular events or conditions, e.g., an application being initiated by a user, an image being selected by the user, and/or one or more other conditions occurring which can be specified in settings read by the method. In some implementations, such conditions can be specified by a user in stored custom preferences of the user.

In one example, a client device can be a camera, cell phone, smartphone, tablet computer, wearable device, or other client device that can receive content input (e.g., image capture) and user input (e.g., using a touchscreen, using gestures, using a mouse or other pointing device, using a keyboard, etc.) by a user to the client device, and can perform the method 200. In another example, a client device or server device can perform the method 200. Some implementations can initiate method 200 based on user input. A user (e.g., operator or end-user) may, for example, have selected the initiation of the method 200 from a user interface, e.g., application user interface or other user interface. In some implementations, method 200 may be implemented by a client device. In some implementations, method 200 may be implemented by a server device.

An image as referred to herein can include a digital image having pixels with one or more pixel values (e.g., color values, brightness values, etc.). An image can be a still image (e.g., still photos, images with a single frame, etc.), a dynamic image (e.g., animations, animated GIFs, cinemagraphs where a portion of the image includes motion while other portions are static, etc.) and a video (e.g., a sequence of images or image frames that may include audio). While the remainder of this document refers to an image as a static image, it may be understood that the techniques described herein are applicable for dynamic images, video, etc. For example, implementations described herein can be used with still images (e.g., a photograph, an emoji, or other image), videos, or dynamic images). Text, as referred to herein, can include alphanumeric characters, emojis, symbols, or other characters.

In block 202, it is checked whether user consent (e.g., user permission) has been obtained to use user data in the implementation of method 200. For example, user data can include images captured by a user using a client devices, images stored or accessed by a user, e.g., using a client device, image metadata, user data related to use of an image sharing application, user data related to use of a messaging application, user data related to use of a financial application, user data related to use of a social networking application, user preferences, user biometric information, user characteristics (identity, name, age, gender, profession, etc.), information about a user's social network and contacts, social and other types of actions and activities, content, ratings, and opinions created or submitted by a user, a user's current location, historical user data, images generated, received, and/or accessed by a user, images viewed or shared by a user, etc. One or more blocks of the methods described herein may use such user data in some implementations.

If user consent has been obtained from the relevant users for which user data may be used in the method 200, then in block 204, it is determined that the blocks of the methods herein can be implemented with possible use of user data as described for those blocks, and the method continues to block 212. If user consent has not been obtained, it is determined in block 206 that blocks are to be implemented without use of user data, and the method continues to block 212. In some implementations, if user consent has not been obtained, blocks are implemented without use of user data and with synthetic data and/or generic or publicly-accessible and publicly-usable data. If user consent has not been obtained, method 200 is not performed.

In block 212 of method 200, selection of a first image is received. For example, a plurality of images, e.g., from an image library of a user, may be displayed on a display screen of a device. In some implementations, image thumbnails may be displayed, and selection of a thumbnail may correspond to selection of the corresponding image. For example, the images or thumbnails may be displayed in a grid configuration, e.g., 3 images per row, 4 images per row, etc.

In some implementations, the images may be grouped by one or more image characteristics, e.g., by a date or time associated with corresponding images, by a location associated with the corresponding images (e.g., geographical location), by image albums that the corresponding images belong to, etc. In some implementations, where the user permits use of facial recognition and/or image tagging that groups images by persons that are depicted in the image, the images may be grouped by persons, e.g., "Andrew and Anika," "Andrew and Joyce," "Anika," etc. In some implementations, the groups may utilize multiple image characteristics or factors, e.g., "Andrew and Anika at Forest Trail," "Yesterday with Joyce," etc.

In some implementations, first user input is received that is indicative of selection of one or more first images. In some implementations, receiving the user input may include detecting a tap or press gesture on an image displayed on a touchscreen, voice input, gaze input, detecting manipulation of an input device (mouse, joystick, trackpad, etc.), etc. A user may select one or more of the plurality of images by selecting a corresponding image element displayed on a screen (e.g., an image thumbnail or other image representation, or a display of the entire image). In some implementations, the images may be scrollable or may be organized into multiple pages or sections such that users can select various and/or additional images of the plurality of images. Upon receiving user selection of one or more first images, the method proceeds to block 214.

In block 214, first image characteristics of the selected images, e.g., one or more first images, are determined. In some implementations, determining the first image characteristics may include retrieving the image characteristics from image metadata stored in association with the first images. In some implementations, determining the first image characteristics may include retrieving the image characteristics from an image database, e.g., from an image library that stores the images and the image characteristics in a database.

In some implementations, the first image characteristics may be determined based on analysis of image content (e.g., pixel values of pixels of the first images) and/or image metadata (e.g., date of capture, location of capture, camera make/model, camera settings, image resolution, image color depth, etc.). In some implementations, the analysis of image content may be performed offline, e.g., prior to receiving user selection of images. For example, the analysis of image content of an image may be performed at a time the image is generated (e.g., captured using a camera, captured as a screenshot, etc.), or added to the library (e.g., downloaded or stored on a device that has the image library).

In some implementations, the first image characteristics may be determined by programmatically analyzing the image. In some implementations, the first image characteristics may include one or more labels associated with the image. In some implementations, the one or more labels may be based on image pixel values and/or image metadata. In some implementations, the one or more labels may include one or more semantic concepts associated with the image. In some implementations, the semantic concepts may be organized in a hierarchy of concepts, e.g., "food→cake→birthday cake," "sports→baseball→equipment→bat," etc., where concepts narrower in scope can be included in concept categories broader in scope. There can be any number of semantic concepts associated with an image. Semantic concepts may be determined based on one or more of detecting one or more objects in the image, image attributes such as focus, illumination level, image composition, color distribution, metadata such as location, time, and other metadata, and other factors. In some implementations, the semantic concepts may be determined using a machine learning model trained to recognize semantic concepts from images.

In some implementations, the image characteristics, e.g., the one or more labels, may be associated with a confidence score. The confidence score may indicate a degree of confidence that the particular label applies to the image. The one or more labels and the corresponding confidence score may be based on programmatically analyzing the image. In some implementations, programmatically analyzing the image may be performed using a trained machine learning model. In some implementations, programmatically analyzing the image may be performed using object detection and recognition techniques. In some implementations, combinations of various image analysis techniques may be used.

In some implementations where the user provides consent, programmatically analyzing the image may include identifying one or more semantic concepts from image pixel data. For example, it may be determined whether the image was taken indoors or outdoors. In another example, the machine learning model may determine whether the image depicts one or more of various objects, e.g., trees, flowers, buildings, river or ocean, mountains, etc. In some implementations, the machine learning model may determine specific characteristics of the objects depicted, e.g., "a red rose," "a twelve-story building," "a coffee shop," "a birthday cake," etc.

In some implementations where the user provides consent, one or more objects in the image may be recognized, e.g., "Taj Mahal," "baseball bat," "ice cream," etc. In implementations where the user provides consent for use of facial detection, it may be determined whether the image depicts one or more persons (e.g., "image has 3 persons" or "image depicts two women"). In implementations where the user provides consent for use of facial recognition techniques, the persons in an image may be recognized, e.g., "Joyce," Andrew," etc.

In some implementations where the user provides consent, image characteristics may be determined from image metadata. For example, such image characteristics may include camera make/model, camera settings (e.g., aperture, use of flash, camera mode, etc.) date and/or time of image capture, location of image capture (if the user permits use of location data).

In some implementations where the user provides consent, one or more semantic concepts may be determined based on objects detected in the image and/or image metadata, e.g., when an image is captured with the flash turned on, the objects depicted include a dining table and food, and the location and time of image capture indicates that the image was captured at nighttime, the semantic concepts may be "dinner" and "indoors." In another example, when an image depicts water and a sailboat, the semantic concept of "sailing" may be associated with the image.

Upon recognition of objects in an image and/or determination of semantic concepts corresponding to the image, one or more labels may be associated with the image. The image characteristics, e.g., the one or more labels, may be stored, e.g., as image metadata in an image file, in a database, etc. For example, the labels associated may be "Joyce; dinner; indoors; home" "hiking trail; Yosemite national park," etc.

In some implementations, image characteristics may include an image type, e.g., "document," "receipt," "screenshot," "photo," etc. determined based on programmatically analyzing the images. In some implementations, image characteristics may include image attributes determined based on programmatically analyzing the image, e.g., "blurry," "dark," etc. Block 214 may be followed by block 216.

In block 216, one or more second images in the image library are identified. In some implementations, the one or more second images may have at least one image characteristic that is the same as or similar to an image characteristic of one or more first image characteristics of the one or more first images selected by the user. For example, if the user selects a first image that is blurry, one or more second images are identified that are each associated with the image characteristic of blurriness.

In another example, if the user selects two images of documents (e.g., an image that depicts text or visual content that is determined to be a document), one or more second images are identified that are each associated with the image characteristic "document." In another example, if the user selects two images that are screenshots (e.g., captures of the content of a display screen of a device), one or more second images are identified that are each screenshots, e.g., associated with the image characteristic "screenshot." In another example, if the user selects an image that depicts two individuals, e.g., Joyce and Andrew, one or more second images are identified that are each associated with image labels for at least one of "Joyce" and "Andrew."

In another example, if one or more of the first images are associated with a location, e.g., "Taj Mahal," one or more second images may be selected that are associated with same or similar location, e.g., "Taj Mahal, "Agra," etc. In some implementations, the one or more second images may be selected such that the location associated with the second images is within a threshold distance of the location associated with the first image. For example, the threshold distance may be a numerical distance, e.g., "5 miles." In some implementations, the one or more second images may be selected based on matching the location, e.g., a city name, a country name, etc. In some implementations, the one or more second images may be selected based on the images depicting one or more of the same characteristics as depicted by a first image at the first location, e.g., a monument, bridge, skyscrapers, etc.

In some implementations, a context of image selection may be determined. For example, it may be determined that the user interface in which the user provides the first user input is associated with generating an image-based creation by one or more devices, e.g., an image collage, a video based on images in the image library, an image album, or a printed publication, e.g., a photo book. In some implementations, the context of image selection can be, or can be based on, an associated target software application, e.g., a messaging application, an image sharing or social networking application, a financial application, etc. from which the user interface for image selection was initiated.

In the implementations in which the context of image selection is determined, identifying the one or more second images may be based on the context. For example, a context can be associated (e.g., prior to block 216) with one or more selection criteria for selecting the second images. For example, if the context is determined as generating a photo book or sharing via an image sharing application, the one or more second images may be selected based on quality criteria, e.g., an image resolution criterion, an image color depth criterion, an image focus criterion, etc., that are associated with that context. In some examples, images that do not meet an image resolution threshold criterion may be excluded from the one or more second images, even if such images have characteristics that match first image characteristics. In another example, if the context is determined as a financial application, images that have certain characteristics, e.g., image type "receipt," "invoice," "financial statement," "document," etc. may be included in the one or more second images, and other images may be excluded.

In some implementations, the one or more second images are selected or filtered based on a number of image characteristics that match the image characteristics of the first images. For example, if a first image depicts "Joyce and Andrew at the beach," second images may be selected based on how many of the three characteristics "Joyce," "Andrew," and "beach" are associated with each of the second images. In one example, if the image library includes image A, image B, and image C that have all three characteristics and further images D, E, and F that have two of the three characteristics, images A, B, and C may be selected as the one or more second images and images D, E, and F may be excluded from the second images. In some implementations, the images A-F are included in the second images and other images, including images that have only one of the three characteristics, are excluded from the second images.

In some implementations, a confidence threshold may be used to filter the one or more second images. For example, if a first image is associated with the characteristic "receipt" with a confidence score of 90%, a second image may be selected that is associated the characteristic "receipt" with at least a confidence score of 90%. In this example, images that have a lower confidence score may be excluded from the one or more second images, even when the images are associated with the characteristics "receipt." In some implementations, a combination of the number of characteristics that match the image characteristics of the first image and confidence scores associated with the characteristics may be used to select the one or more second images. In some implementations, each image characteristics may be weighted to determine the one or more second images. For example, some characteristics, e.g., a label such as "Taj Mahal" or "Joyce," may be assigned a higher weight than other characteristics, e.g., "outdoors."

In some implementations, when users provide consent for use of user data related to image selections and image-based creations generated by the user, such data may be used to select the one or more second images. For example, if the user has previously generated printed publications, e.g., photo books, that include photos of flowers, one or more second images that depict flowers may be included. In this example, images that were included in a prior photo book may be excluded, e.g., if the user data indicates that user periodically generates photo books that include recently captured images.

In another example, if the user has previously ignored suggestions to select certain types of photos, e.g., photos that do not depict a human face, such images may be excluded from the one or more second images. In another example, if the user data indicates that the user generates picture collages that include images of certain individuals, e.g., family members, pets, etc., images that depict the individuals may be selected in the one or more second images, and images that do not depict the individuals may be excluded. In some implementations, images with certain characteristics, e.g., high blurriness, dark image, low quality image, archived image, etc. may be excluded from the one or more second images, even when such images have characteristics that match the one or more first images.

In some implementations, e.g., when the user indicates that the image-based creation is a video, the one or more second images may include video clips or images with motion, that may be excluded for other image-based creations, e.g., image collage. In some implementations, video clips may be selected based on non-visual parameters, e.g., a length of the video clip, semantic concepts or labels determined audio portion of the video clip, etc. Block 216 may be followed by block 218.

In block 218, a user interface is caused to be displayed. For example, the user interface may be displayed by any of client device 120-124. The user interface may include the one or more second images. For example, the user interface may be displayed, e.g., as a card or overlay that includes a display of a grid of images. In some implementations, the one or more second images may be displayed with a displayed indication that these images are suggested selections, e.g., displayed in a "Suggestions" section of the user interface. The one or more second images are user selectable. In some implementations, the user interface may also include other images that are user selectable, e.g., recent images that were captured or received within a particular time period just prior to a current time, that are not included in the one or more second images. In some implementations, the other images may be grouped in a section of the user interface separate from the "Suggestions" section, e.g., a "Recent" section. In some implementations, images that are currently selected may be displayed in a section of the user interface, e.g., a "selection tray" section. The "selection tray" may be distinct from other parts of the user interface that include the first images and the one or more additional images that are available for selection by the user. Block 218 may be followed by block 220.

In block 220, it is determined whether further image selections are received. For example, the further image selections may be received via second user input. In some implementations, the images indicated by the further image selections may include at least one of the one or more second images. In some implementations, the images indicated by the further image selections may include at least one of the one or more recent images. If further image selections are received, the method proceeds to block 214. In some implementations, one or more third images in the image library may be identified. For example, the one or more third images may be identified based on determining characteristics of a selected image from the further image selections, e.g., from the one or more second images and/or from other images displayed in the user interface.

The one or more third images may be identified by matching the characteristics of the first images (selected in the first user input) and the images selected via second user input. For example, the one or more third images may be identified such that each of the third images has at least one characteristic that matches a characteristic of the selected images, e.g., at least one characteristic that is associated with one or more of the first images and associated with one or more of the second images. For example, if a first image (selected by first user input) depicts "Joyce and Andrew at the beach" (e.g., is associated with the labels "Joyce," "Andrew," and "beach") and the selected image (selected by second user input) depicts "Joyce and Andrew," the one or more third images may be identified as images in the image library that depict both Joyce and Andrew. In this example, the "beach" characteristic is not considered while identifying the third images.

In different implementations, the one or more third images may be selected using techniques similar to those used for selecting the one or more second images. In the implementations where one or more third images are identified, the user interface may be updated to include the one or more third images. For example, updating the user interface may include updating the "Suggestions" section to display the one or more third images in place of, or in addition to, the one or more second images. In some implementations. upon identifying the one or more third images, the "Suggestions" section may be displayed with a higher priority than other sections (e.g., "Recent") of the user interface.

In some implementations, further user input indicative of additional selections of images may be received (e.g., via iterations of blocks 214-220) and in response, the user interface may be updated to include additional images, based on matching image characteristics of images in the image library with image characteristics of images selected by the user input. When no further image selections are received, block 220 may be followed by block 222.

In block 222, user selections of one or more actions (e.g., operations) are received, e.g., via the user interface. The user-selected actions are performed, using the user selected images. For example, the user may indicate that an image-based creation (e.g., content creation) be generated based on the selected images, e.g., image selections indicated by the first user input, the second user input, and subsequent user inputs, if any. For example, the image-based creation may include an image collage, a video that depicts the selected images, e.g., as a short video clip or slideshow, an image album that includes the selected images, or a printed publication, e.g., a photo book, that includes the selected images.

In another example, the one or more actions selected by the user may be to provide the selected images to a target software application, e.g., a messaging application, an image-sharing application, a social networking application, a financial application, etc. In this example, the selected images are provided to the target software application, e.g., via an application programming interface (API). In some implementations, the selected images may be modified (e.g., automatically enhanced, cropped, reduced in file size, etc.) prior to providing the images to the target software application.

In some implementations, the one or more actions selected by the user may be actions for an image library application, e.g., to perform modifications to the images in the image library. For example, if the user selects images that include duplicates of each other or of other images (e.g., select images that all depict similar subject matter to one or more other selected images, and are associated with similar metadata, or depict similar subject matter to one or more other images in the library), the action may be to delete duplicates. For example, the duplicate images having image characteristics that score less than the other duplicate images can be deleted, e.g., based on visual characteristics such as blurriness, exposure, color noise, object position with respect to image borders, etc. In another example, if the user selects images that each have one or more common characteristics (e.g., "dark," "not enhanced"), the action may be to perform an automatic enhancement of the selected images, e.g., by modifying pixel values using image enhancement techniques, e.g., applying image filters, modifying the images using a machine learning model trained for image enhancement, etc.

In some implementations, the action may be to archive the selected images, which causes the selected images to be hidden from one or more views, e.g., a main view, of images of the image library. For example, a label associated with the selected images can be updated to indicate that the selected images are archived. Archived images can be displayed if a command is received, e.g., via user input, to view archived images. In some implementations, image metadata or labels associated with images that are archived may be updated to indicate that the image is archived. Such metadata or labels may be used, e.g., when generating the main view of images in the image library, to exclude the archived images from the main view.

In some implementations, the one or more actions may include actions that correspond to a suggested action element displayed in the user interface. In these implementations, the suggested action element may be determined based on the selected images, e.g., one or more of the first images and one or more of the second images. In some implementations, the action associated with the suggested action element may include one or more of archiving the selected images, deleting the selected images (e.g., removing the selected images from the image library, deleting the images from storage, etc.), or performing an automatic enhancement of the selected images.

For example, it may be determined that the selected images have an image characteristic of "blurry." Based on the determination, a suggested action element may be displayed, e.g., "delete all blurry." If the user selects the suggested action element, the corresponding action may be performed, e.g., by the device. In some implementations, additional images that match the selected images, e.g., other blurry images in the library that are taken at or near a same location and at a similar time as the selected images may be included and the selected action is performed on the user selected images and the additional images that match the selected images.

While method 200 has been described with reference to various blocks in FIG. 2, it may be understood that techniques described in this disclosure may be performed without performing some of the blocks of FIG. 2. In some implementations, one or more of the blocks illustrated in FIG. 2 may be combined. For example, two or more of blocks 214, 216, and 218 may be combined. In various implementations, some of the blocks of method 200 may be performed in parallel or in an order different from that illustrated in FIG. 2. In some implementations, method 200 is performed by a client device, e.g., one or more of client devices 120-124. In some implementations, method 200 is performed by a service device, e.g., the server device 104. In some implementations, method 200 is performed by a combination of client and server devices. For example, in some implementations, blocks 202, 204, 206, 212, 218, and 220 are performed by a client device, and blocks 214, 216, and 222 are performed by the server device. For example, such approach may be useful when the client device 120 has limited capability to determine image characteristics, e.g., by programmatically analyzing images, has limited storage capacity to store image data, etc.

Figure 3:
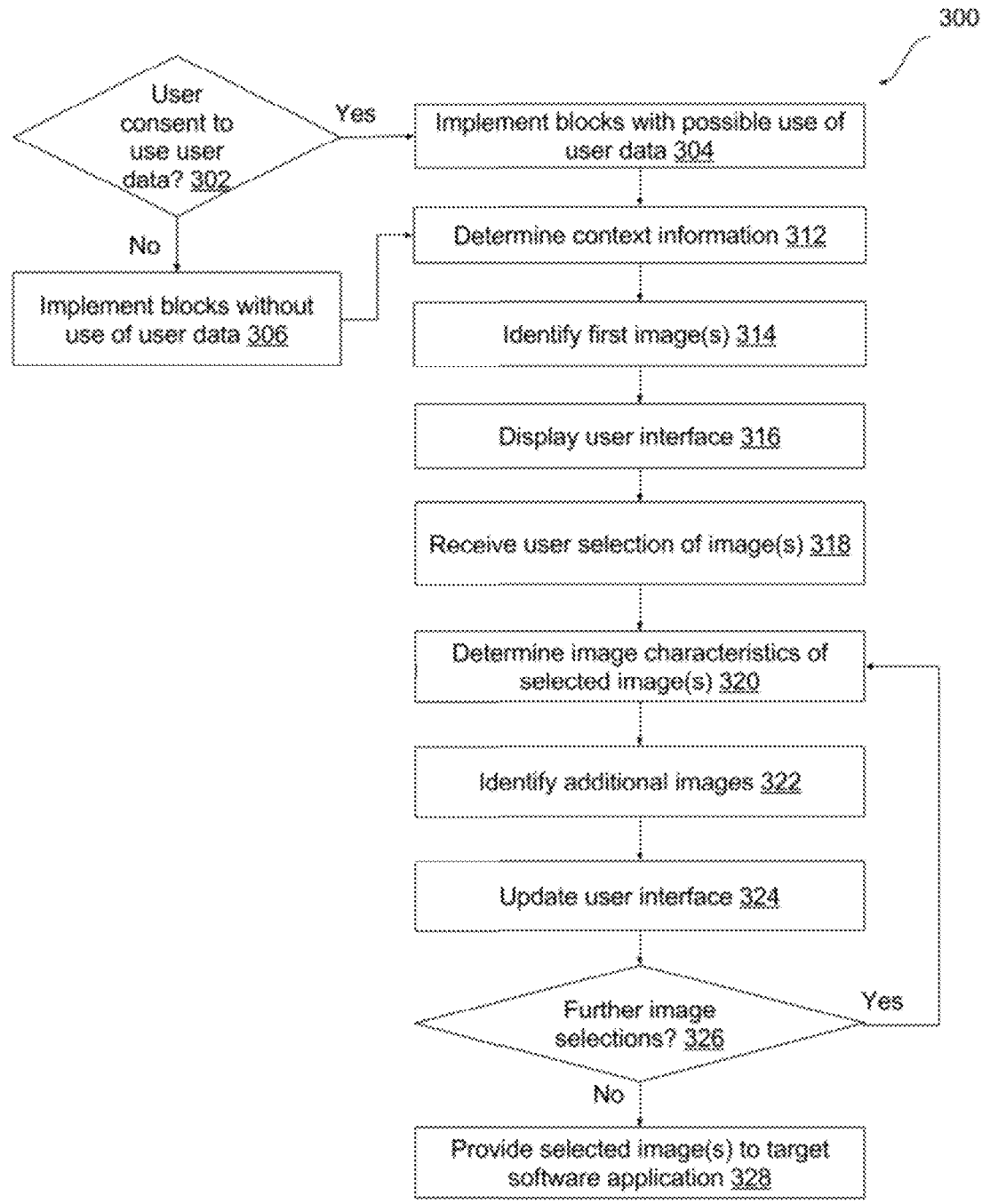
FIG. 3 is a flow diagram illustrating an example method to provide image selection suggestions, according to some implementations.

FIG. 3 is a flow diagram illustrating one example of a method 300 to provide image selection suggestions, according to some implementations. In some implementations, method 300 can be implemented, for example, on a server system 102 as shown in FIG. 1. In some implementations, some or all of the method 300 can be implemented on one or more client devices 120, 122, 124, or 126 as shown in FIG. 1, one or more server devices, and/or on both server device(s) and client device(s). In described examples, the implementing system includes one or more digital processors or processing circuitry ("processors"), and one or more storage devices (e.g., a database 106 or other storage). In some implementations, different components of one or more servers and/or clients can perform different blocks or other parts of the method 300. In some examples, a first device is described as performing blocks of method 300. Some implementations can have one or more blocks of method 300 performed by one or more other devices (e.g., other client devices or server devices) that can send results or data to the first device.

In some implementations, the method 300, or portions of the method, can be initiated automatically by a system. In some implementations, the implementing system is a first device. For example, the method (or portions thereof) can be periodically performed, or performed based on one or more particular events or conditions, e.g., an application being initiated by a user, an image being selected by the user, and/or one or more other conditions occurring which can be specified in settings read by the method. In some implementations, such conditions can be specified by a user in stored custom preferences of the user.

In one example, a client device can be a camera, cell phone, smartphone, tablet computer, wearable device, or other client device that can receive content input (e.g., image capture) and user input (e.g., using a touchscreen, using gestures, using a mouse or other pointing device, using a keyboard, etc.) by a user to the client device, and can perform the method 300. In another example, a client device or server device can perform the method 300. Some implementations can initiate method 300 based on user input. A user (e.g., operator or end-user) may, for example, have selected the initiation of the method 300 from a user interface, e.g., application user interface or other user interface. In some implementations, method 300 may be implemented by a client device. In some implementations, method 300 may be implemented by a server device.

In block 302, it is checked whether user consent (e.g., user permission) has been obtained to use user data in the implementation of method 300. For example, user data can include images captured by a user using a client devices, images stored or accessed by a user, e.g., using a client device, image metadata, user data related to use of an image sharing application, user data related to use of a messaging application, user data related to use of a financial application, user data related to use of a social networking application, user preferences, user biometric information, user characteristics (identity, name, age, gender, profession, etc.), information about a user's social network and contacts, social and other types of actions and activities, content, ratings, and opinions created or submitted by a user, a user's current location, historical user data, images generated, received, and/or accessed by a user, images viewed or shared by a user, etc. One or more blocks of the methods described herein may use such user data in some implementations.

If user consent has been obtained from the relevant users for which user data may be used in the method 300, then in block 304, it is determined that the blocks of the methods herein can be implemented with possible use of user data as described for those blocks, and the method continues to block 312. If user consent has not been obtained, it is determined in block 306 that blocks are to be implemented without use of user data, and the method continues to block 312. In some implementations, if user consent has not been obtained, blocks are implemented without use of user data and with synthetic data and/or generic or publicly-accessible and publicly-usable data. If user consent has not been obtained, method 300 is not performed.

In block 312 of method 300, context information indicative of a target software application is determined. For example, when method 300 is implemented as part of an image library application that enables a user to generate image-based creations, e.g., an image album, an image collage, a video, or a printed publication, the context information may include a type of image creation.

In another example, when method 300 is implemented as part of an image library application that supports interaction with other applications, e.g., via an application programming interface (API), determining the context information may include determining an application type of application that invokes the image library application, e.g., an image sharing application (e.g., a standalone image sharing application, a social networking application, etc.) a financial application (e.g., an expense management application, an invoicing application, etc.), a messaging application (e.g., a chat or instant messaging application, an e-mail application, a collaboration application, etc.) In this example, the application that invokes the image library application is referred to as a target software application.

Further, in some implementations, determining the context information may include receiving a number of images to be selected, e.g., one image, two images, etc. from the target software application. In another example, such context information may include a type of images that are to be selected, e.g., images with motion (e.g., video clips), images of a particular aspect ratio and/or orientation (e.g., square, portrait orientation, landscape orientation, etc.), still images, dynamic images, etc.

In another example, if user consent has been obtained, determining the context information may include receiving identification information of participants (e.g., user identifiers such as usernames, login IDs, et.) in a messaging conversation (e.g., e-mail recipients), characteristics of prior images that have been shared via an image sharing application (e.g., landscape images, food images, selfies, etc.), etc. In another example, the context information may include a user activity conducted using the target software application, such as a financial application, e.g., submitting an expense report, generating an invoice, etc.

In some implementations, the target software application may provide the context information via the API. In some implementations, if user consent has been obtained, the context information may be provided as one or more image characteristics, e.g., "selfie," "receipt," "vacation," etc. that can be matched with image characteristics associated with images in an image library of a user. Such image characteristics can be based on image content (e.g., depicted image features) and/or image metadata (e.g., time of capture, location of capture, attributes and settings of the capturing camera, etc.), if user consent has been obtained. In some implementations, the context information may be provided as semantic concepts, e.g., "expense report," "chat conversation with Andrew," etc.

When the user provides consent, the context information may include an application context from the target software application. For example, the application context may include a summary of conversation or semantic concepts associated with a conversation conducted via a messaging application, a time period of an expense report under preparation in the financial application, etc. For example, the application context may include "this conversation is about a vacation in Bali," "expense report for November 2017," etc. Block 312 may be followed by block 314.

In block 314, one or more first images are identified based on the context information. For example, the first images may be based on matching the context information with image characteristics of images in the image library. In some implementations, the matching may be based on an application type of the target application. For example, particular image characteristics can be associated, prior to block 314, with particular types of applications. For example, if the application type is "financial application," images that are associated with a label indicating the images are a "receipt," "document," "screenshot," etc. may be selected as the one or more first images, and images having other characteristics (e.g., labels), e.g., "photo," "video," etc. may be excluded.

In some implementations, the first images may be based on matching image characteristics and/or semantic concepts specified in the context information with image characteristics of images in the image library. For example, if the application type is a messaging application and the context information includes identification information of participants in a messaging conversation, e.g., context information specifies that a chat conversation provided by a messaging application involves the users Andrew and Joyce, images that depict at least one of Andrew and Joyce may be selected as the first images.

In another example, if the application context specifies that a chat conversation provided by a messaging application is about a vacation in Bali, one or semantic concepts are determined based on the application context. For example, the semantic concepts may include "vacation," "Bali," "beach," "Indonesia," "temple," etc. Images that are associated with the semantic concepts determined from or specified in the application context may be selected as the first images. In another example, if the context information specifies an expense report for November 2017, an image of a receipt with an associated timestamp that corresponds to November 2017 may be selected as a first image. Block 314 may be followed by block 316.

In block 316, a user interface that includes the first images is displayed. For example, the user interface may be displayed by any of client device 120-124. The user interface enables the user to select one or more of the first images, similar to the user interface described above with reference to block 218. Block 316 may be followed by block 318.

In block 318, user selection of one or more of the displayed images (e.g., first images) is received. For example, block 318 can be similar to block 212 of FIG. 2. Block 318 may be followed by block 320.

In block 320, image characteristics of the images selected in block 318 are determined, e.g., in a manner similar to block 214 described above. Block 320 may be followed by block 322.

In block 322, one or more additional images are identified. In some implementations, the additional images may be identified based on the image characteristics determined in block 320. For example, if the user selection corresponds to images associated with the labels "Bali" and "Andrew," additional images are identified that have at least one of the labels. In some implementations, identifying the additional images is based on image characteristics determined in block 320 and on the context information, e.g., similar to block 314 above. Block 322 may be followed by block 324.

In block 324, the user interface is updated to include the one or more additional images. For example, the one or more additional images may be displayed in place of, or in addition to the first images. In some implementations, the updated user interface may include a section, e.g., a "selection tray" section, that includes the images selected by the user. The "selection tray" may be distinct from other parts of the user interface that include the first images and the one or more additional images that are available for selection by the user. Other features can be provided similarly as described for block 218 of FIG. 2. Block 324 may be followed by block 326.

In block 326, it is determined if further image selections are received from the user, e.g., from the images displayed in the updated user interface. If further image selections are received, the method proceeds to block 320, where image characteristics of the additional images selected by the user are determined. Blocks 320-326 may be repeated to provide additional images selection suggestions to the user. If no further image selections are received, the method proceeds to block 328.

In block 328, the images selected by the user are provided to the target software application. For example, if the target software application is the image library application, the selected images may be provided as images to be utilized for an image-based creation. In another example, if the target software application is an image sharing or messaging application, the selected images may be provided such that the images are available for sending to one or more other devices (e.g., over a network) via the image sharing or messaging application. In some implementations, the selected images may be processed, e.g., automatically enhanced, cropped, compressed, converted into a different format, prior to providing the image to the target software application. In some implementations, the processing of the image may be based on the context information received from the target software application.

While method 300 has been described with reference to various blocks in FIG. 3, it may be understood that techniques described in this disclosure may be performed without performing some of the blocks of FIG. 3. In some implementations, one or more of the blocks illustrated in FIG. 3 may be combined. For example, two or more of blocks 314, 316, and 318 may be combined. In another example, two or more of blocks 320, 322, and 324 may be combined. In various implementations, some of the blocks of method 300 may be performed in parallel or in an order different from that illustrated in FIG. 3.

In some implementations, method 300 is performed by a client device, e.g., one or more of client devices 120-124. In some implementations, method 300 is performed by a service device, e.g., the server device 104. In some implementations, method 300 is performed by a combination of client and server devices. For example, in some implementations, blocks 302, 304, 306, 312, 318, 326, and 328 are performed by a client device, and blocks 314, 316, 320, 322, and 324 are performed by the server device. For example, such approach may be useful when the client device 120 has limited capability to determine image characteristics, e.g., by programmatically analyzing images, has limited storage capacity to store image data, etc.

Figure 4:
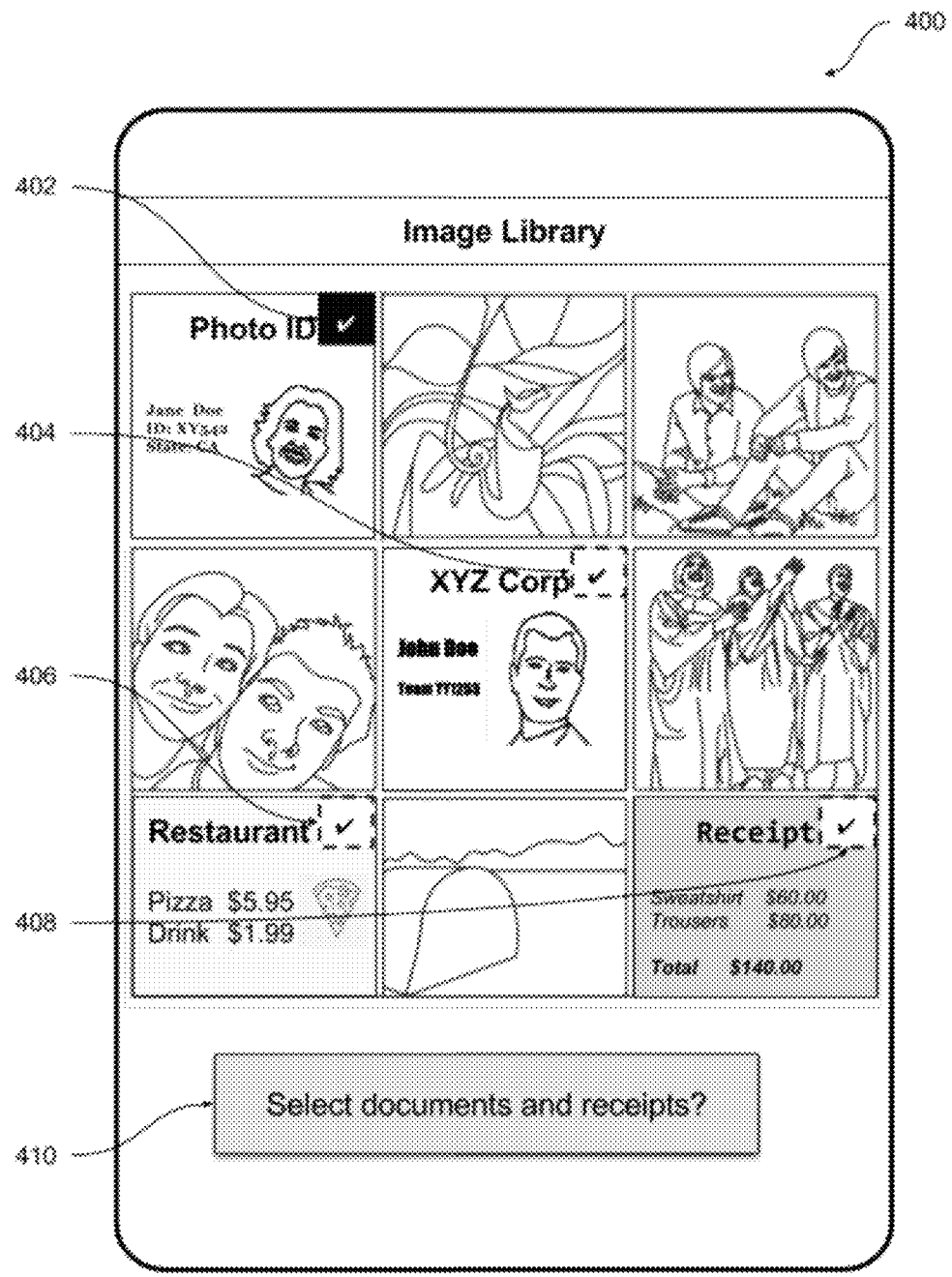
FIG. 4 is a diagrammatic illustration of an example user interface 500 that includes image selection suggestions, according to some implementations.

FIG. 4 is a diagrammatic illustration of an example user interface 400 that includes image selection suggestions, according to some implementations. In various implementations, user interface 400 can be displayed by a display device, e.g., by a display screen of a client device 120, 122, 124, and/or 126 of FIG. 1, or a server system 102 in some implementations.

As illustrated in FIG. 4, a portion of an image library of a user is displayed in a user interface. In the example illustrated in FIG. 4, nine images from the image library are shown. While FIG. 4 shows three rows of images with three square images per row, any number of rows and columns in a grid can be used, based on the available screen space. Further, different implementations may display the images in other configurations or arrangements. In some implementations, more or less images from the library might be shown. In some implementations, the images may be organized in a particular order, e.g., reverse chronological order, based on a timestamp associated with the images.

In the example illustrated in FIG. 4, the user has selected the leftmost image in the top row, as illustrated by a check mark 402 on the image. As can be seen from FIG. 4, the image selected by the user (e.g., first image) is of a photo ID ("Jane Doe"). Using the techniques described herein, one or more suggested image selections (e.g., second images) based on the user-selected image are displayed in the user interface. For example, the suggested image selections are indicated by corresponding check marks 404, 406, and 408 on three other images in the user interface. The suggested image selection corresponds to an image of a photo ID ("John Doe" of "XYZ Corp") and two images of receipts. The suggested image selections in this example are based on matching image characteristics of the first image (e.g., "document," "identity card,") with those of other images in the image library.

User interface 400 further shows a suggested action element 410. In the example illustrated in FIG. 4, the suggested action is to "select documents and receipts." If the user selects the suggested action element 410, other images from the user's image library that are documents are receipts are automatically selected, based on associated image characteristics. For example, automatically selected images can be displayed with check marks similar to check marks 404, 406, and 408 if such images are scrolled or otherwise commanded via user input to be displayed in the view of the user interface 400. In some implementations, such automatically selected images can be displayed in a display area of the user interface that is separate from the display of the images in the image library. In some implementations, other or additional actions, e.g., "archive selected images," "auto-enhance selected images," "delete selected images," etc. may be shown in the suggested action element.

In some implementations, the suggested actions may be based on the image characteristics, e.g., different particular suggested action(s) can be associated with respective particular image characteristics. For example, if the user has selected images that are blurry, a suggested action may be to delete the images. In another example, if the user has selected images that are dark, a suggested action may to apply a brightness or contrast enhancement. In some implementations, a suggested action may be a compound action, e.g., "select images, apply image filter, and share images via messaging application." If the user selects the suggested action element 410, the corresponding action is automatically performed.

User interface 400 enables the user to select images with reduced effort and with reduced consumption of device resources including memory, processing resources, and power. For example, instead of the user having to select each blurry image manually with many scrolling and searching operations on the device, the user interface may enable the user to approve presented suggested selections with simple and reduced device operations. Further, other images in the image library that are not displayed in user interface 400 but that have characteristics that match the user-selected image can be selected without the user having to scroll through images and manually select each image.

Figure 5A:
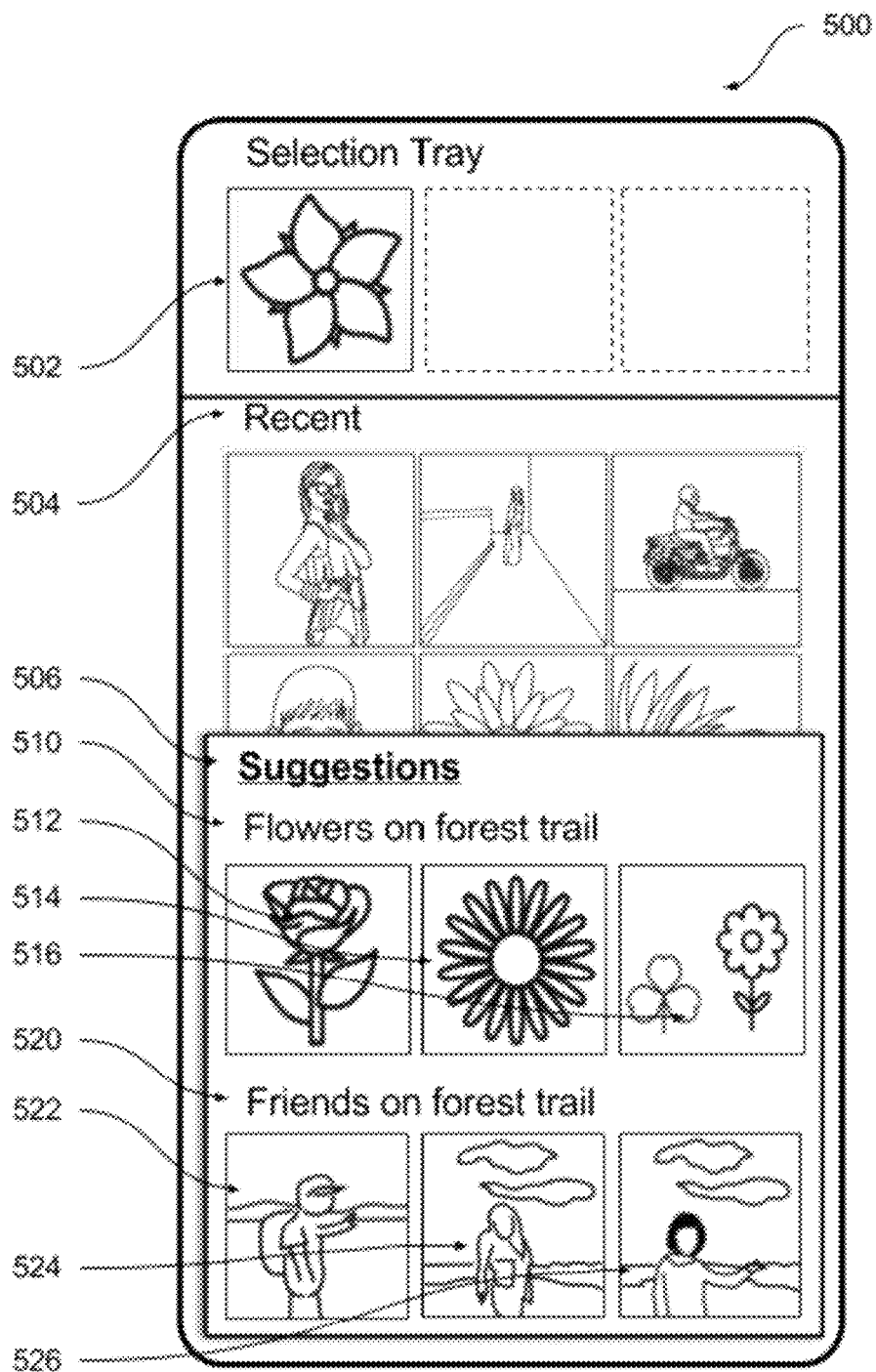
FIG. 5A is a diagrammatic illustration of an example user interface 400 that includes image selection suggestions, according to some implementations.

FIG. 5A is a diagrammatic illustration of an example user interface 500 that provides image selection suggestions, according to some implementations. In various implementations, user interface 500 can be displayed by a display device, e.g., by a display screen of a client device 120, 122, 124, and/or 126 of FIG. 1, or a server system 102 in some implementations.

As illustrated in FIG. 5A, user interface 500 includes a selection tray that includes a user selected image 502, and two blank spots indicating that additional images can be selected and added to the tray. User interface 500 includes images that the user can select from. For example, the user can select one or more recent images from the "Recent" section (504) of the user interface. In some implementations, images in the "Recent" section may be organized in a descending order of time, based on a capture timestamp associated with images in the user's image library.

User interface 500 further includes suggestion 506 that includes suggested image selections determined using techniques described herein. In the example illustrated in FIG. 5, the suggested image selections are displayed in the form of a "Suggestions" card, overlaid atop the "Recent" section 504. In different implementations, suggested image selections may be displayed in different sections of the user interface, check marks or other visual indicators may be used to indicate suggested image selections, etc. In some implementations, suggested image selections may be displayed in a prioritized section of the user interface, e.g., near the selection tray.

In the example illustrated in FIG. 5A, the user has selected image 502 of a flower. Based on the user selection, other images in the image library of the user having characteristics that match one or more characteristics of image 502 are included in suggestions 506. For example, other images of flowers that were captured at a location similar to that associated with image 502 may be displayed, e.g., images 512, 514, and 516. In the example shown in FIG. 5, a summary based on the matching characteristics, "Flowers on forest trail" is shown as a section header 510 in the suggestions card. A second section, with the header "Friends on forest trail" (520) includes additional image suggestions, images 522, 524, and 526. The additional image suggestions are based on the associated location being "forest trail." In different implementations, any number of image suggestions may be provided. User interface 500 enables the user to select one or more images from the Recent section 504 and/or from the Suggestions card 506.

In some implementations, the image suggestions may be organized (e.g. grouped) in the user interface based on a degree of match with images already selected by the user, e.g., image 502. For example, images 512-516 are shown in a first portion of suggestions card 506 since the images include similar subject matter as the selected image 502 and were captured at the forest trail. Images 522-526 are shown in a second portion of suggestions card 506, since the images were captured on the forest trail, but are dissimilar from the selected image 502 since the images do not depict flowers.

Figure 5B:
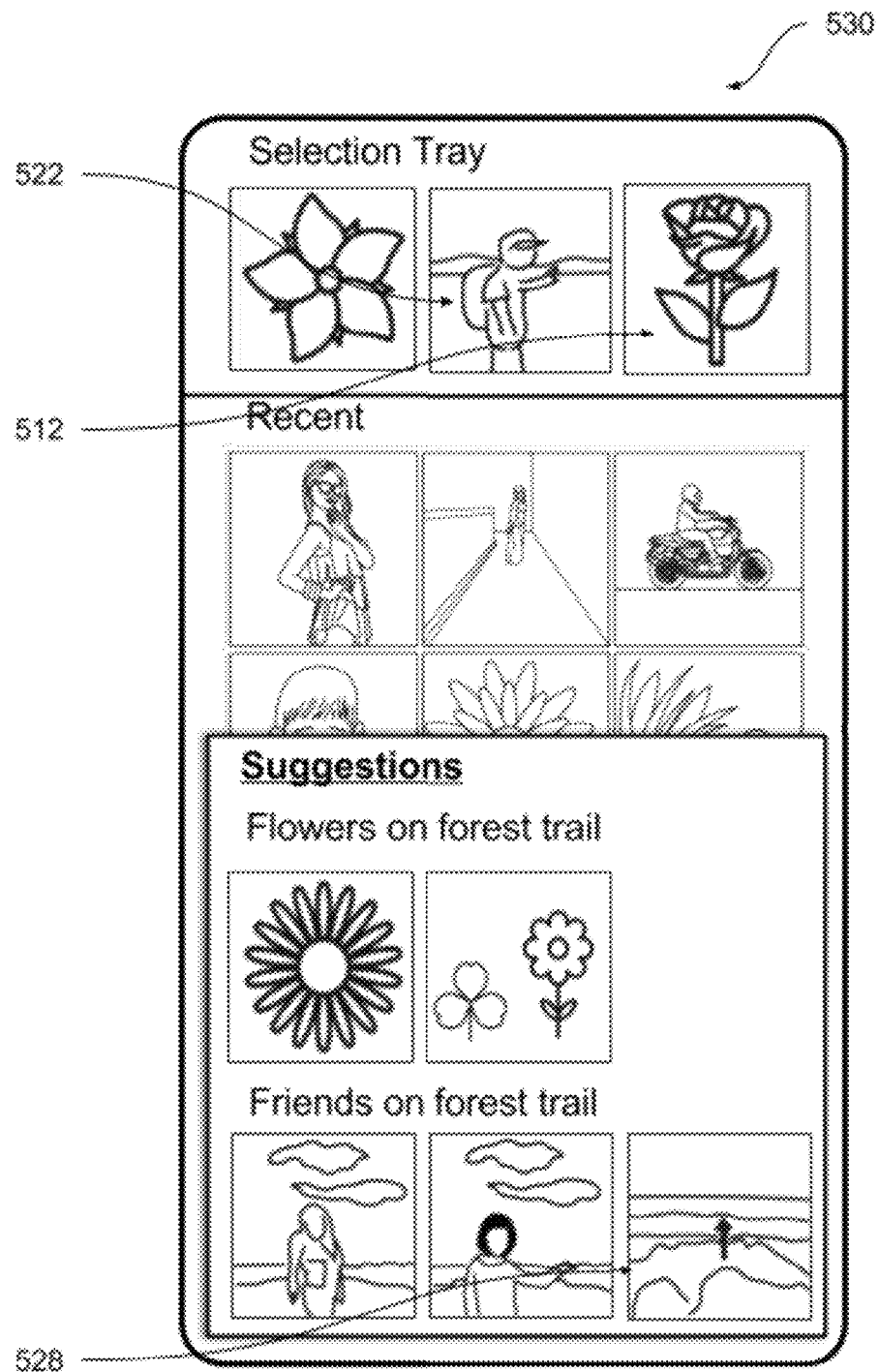
FIG. 5B is a diagrammatic illustration of another example user interface 530 that includes image selection suggestions, according to some implementations.

FIG. 5B is a diagrammatic illustration of an example user interface 530 that provides image selection suggestions, according to some implementations. For example, user interface 530 may be displayed after the user has selected images 522 and 512 via user interface 500. The additional selected images are shown as part of the selection tray. The images 522 and 512 are removed from the suggestions cards. An additional image 528 is added to the suggestions card, e.g., based on matching image characteristics of images in the image library with selected images 502, 512, and 522.

Figure 5C:
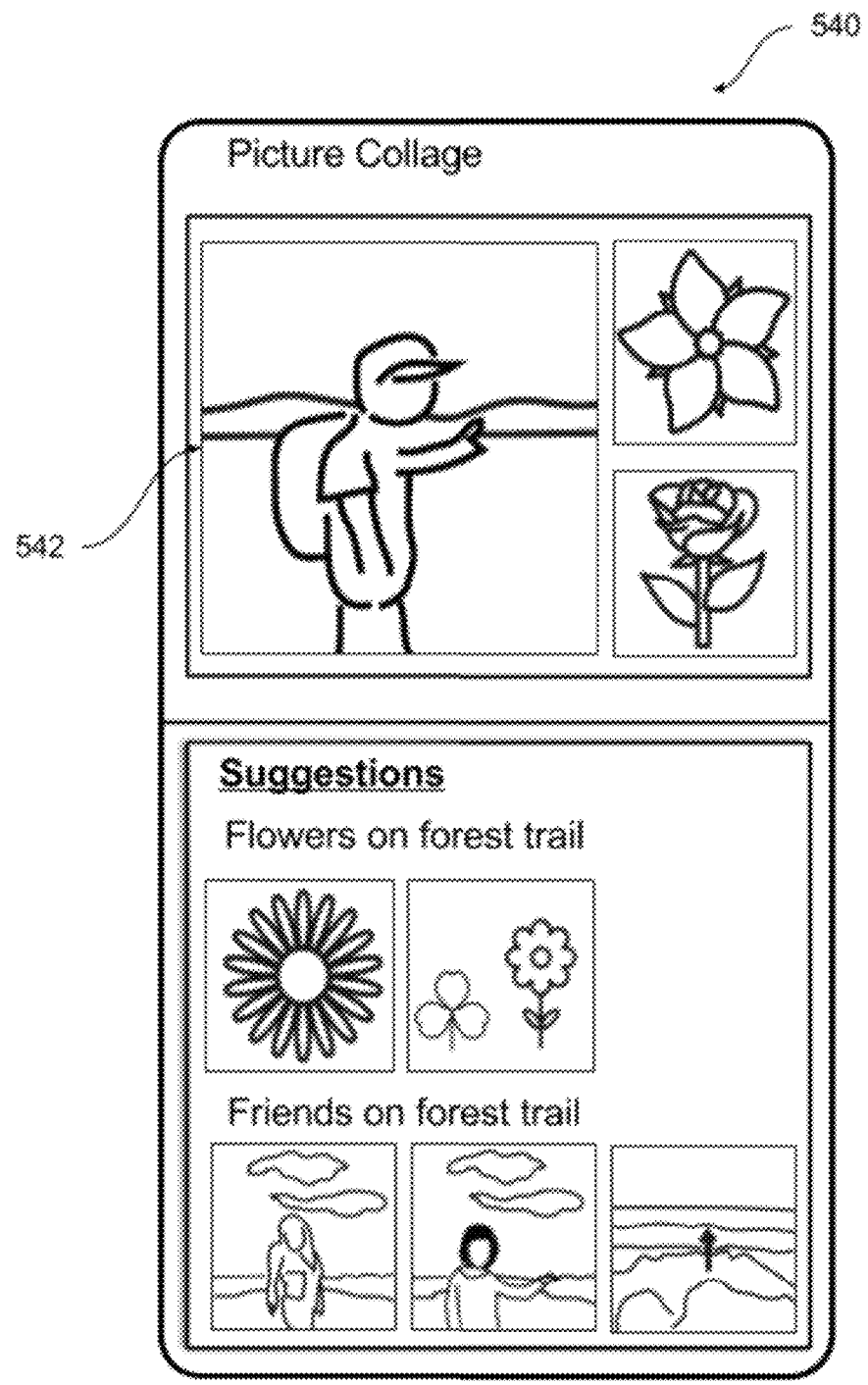
FIG. 5C is a diagrammatic illustration of another example user interface 540 that includes an image creation and image selection suggestions, according to some implementations.

FIG. 5C is a diagrammatic illustration of an example user interface 540 that provides image selection suggestions, according to some implementations. As shown in FIG. 5C, an image-based creation, e.g., picture collage 542 has been generated based on images selected by the user, e.g., images 502, 512, and 522. User interface 540 includes suggestion card with one or more suggested images. For example, user interface 540 may enable the user to select one or more of the suggested images and add the images to the picture collage, e.g., by dragging and dropping images from the suggestions card into the picture collage.

Figure 6:
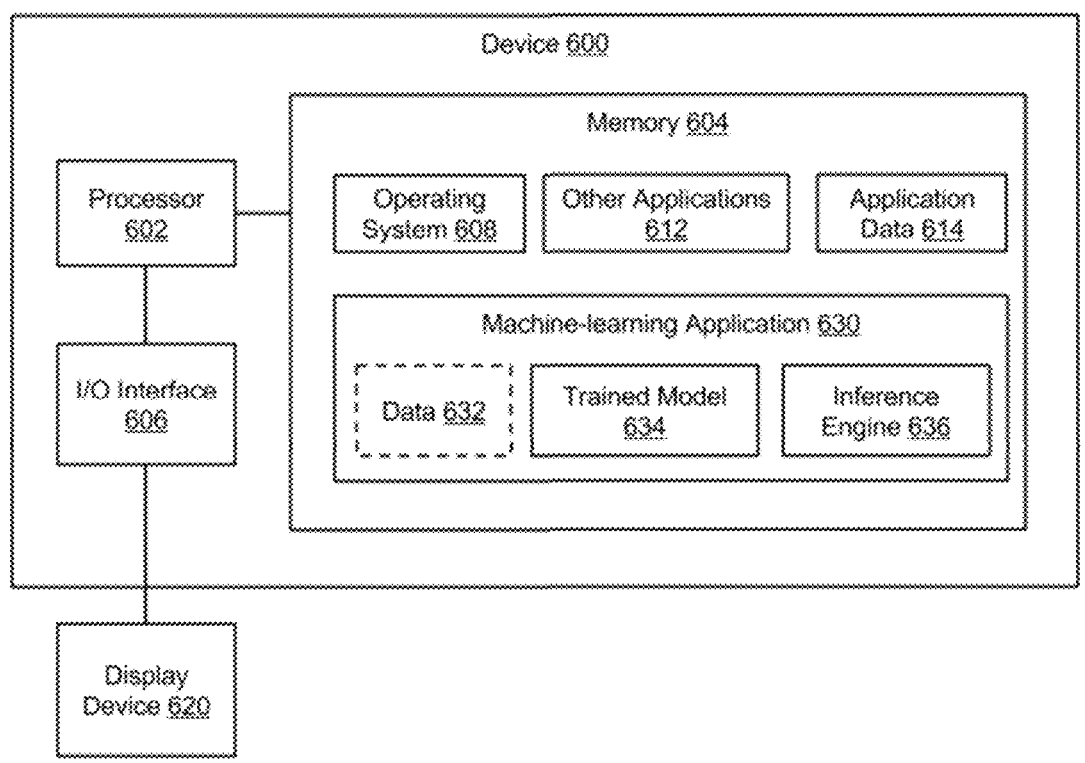
FIG. 6 is a block diagram of an example device which may be used for one or more implementations described herein.

FIG. 6 is a block diagram of an example device 600 which may be used to implement one or more features described herein. In one example, device 600 may be used to implement a client device, e.g., any of client devices 115 shown in FIG. 1. Alternatively, device 600 can implement a server device, e.g., server 101. In some implementations, device 600 may be used to implement a client device, a server device, or both client and server devices. Device 600 can be any suitable computer system, server, or other electronic or hardware device as described above.

One or more methods described herein can be run in a standalone program that can be executed on any type of computing device, a program run on a web browser, a mobile application ("app") run on a mobile computing device (e.g., cell phone, smart phone, tablet computer, wearable device (wristwatch, armband, jewellery, headwear, virtual reality goggles or glasses, augmented reality goggles or glasses, head mounted display, etc.), laptop computer, etc.). In one example, a client/server architecture can be used, e.g., a mobile computing device (as a client device) sends user input data to a server device and receives from the server the final output data for output (e.g., for display). In another example, all computations can be performed within the mobile app (and/or other apps) on the mobile computing device. In another example, computations can be split between the mobile computing device and one or more server devices.

In some implementations, device 600 includes a processor 602, a memory 604, and input/output (I/O) interface 606. Processor 602 can be one or more processors and/or processing circuits to execute program code and control basic operations of the device 600. A "processor" includes any suitable hardware system, mechanism or component that processes data, signals or other information. A processor may include a system with a general-purpose central processing unit (CPU) with one or more cores (e.g., in a single-core, dual-core, or multi-core configuration), multiple processing units (e.g., in a multiprocessor configuration), a graphics processing unit (GPU), a field-programmable gate array (FPGA), an application-specific integrated circuit (ASIC), a complex programmable logic device (CPLD), dedicated circuitry for achieving functionality, a special-purpose processor to implement neural network model-based processing, neural circuits, processors optimized for matrix computations (e.g., matrix multiplication), or other systems. In some implementations, processor 602 may include one or more co-processors that implement neural-network processing. In some implementations, processor 602 may be a processor that processes data to produce probabilistic output, e.g., the output produced by processor 602 may be imprecise or may be accurate within a range from an expected output. Processing need not be limited to a particular geographic location, or have temporal limitations. For example, a processor may perform its functions in "real-time," "offline," in a "batch mode," etc. Portions of processing may be performed at different times and at different locations, by different (or the same) processing systems. A computer may be any processor in communication with a memory.

Memory 604 is typically provided in device 600 for access by the processor 602, and may be any suitable processor-readable storage medium, such as random access memory (RAM), read-only memory (ROM), Electrical Erasable Read-only Memory (EEPROM), Flash memory, etc., suitable for storing instructions for execution by the processor, and located separate from processor 602 and/or integrated therewith. Memory 604 can store software operating on the server device 600 by the processor 602, including an operating system 608, machine-learning application 630, other applications 612, and application data 614. Other applications 612 may include applications such as a data display engine, web hosting engine, image display engine, notification engine, social networking engine, etc. In some implementations, the machine-learning application 630 and other applications 612 can each include instructions that enable processor 602 to perform functions described herein, e.g., some or all of the methods of FIGS. 2 and 3.

Other applications 612 can include, e.g., image editing applications, media display applications, communication applications, web hosting engines or applications, mapping applications, media sharing applications, etc. One or more methods disclosed herein can operate in several environments and platforms, e.g., as a stand-alone computer program that can run on any type of computing device, as a web application having web pages, as a mobile application ("app") run on a mobile computing device, etc.

In various implementations, machine-learning application may utilize Bayesian classifiers, support vector machines, neural networks, or other learning techniques. In some implementations, machine-learning application 630 may include a trained model 634, an inference engine 636, and data 632. In some implementations, data 632 may include training data, e.g., data used to generate trained model 634. For example, training data may include any type of data such as text, images, audio, video, etc. Training data may be obtained from any source, e.g., a data repository specifically marked for training, data for which permission is provided for use as training data for machine-learning, etc. In implementations where one or more users permit use of their respective user data to train a machine-learning model, e.g., trained model 634, training data may include such user data. In implementations where users permit use of their respective user data, data 632 may include permitted data such as images (e.g., photos or other user-generated images), communications (e.g., e-mail; chat data such as text messages, voice, video, etc.), documents (e.g., spreadsheets, text documents, presentations, etc.)

In some implementations, data 632 may include collected data such as map data, image data (e.g., satellite imagery, overhead imagery, etc.), game data, etc. In some implementations, training data may include synthetic data generated for the purpose of training, such as data that is not based on user input or activity in the context that is being trained, e.g., data generated from simulated conversations, computer-generated images, etc. In some implementations, machine-learning application 630 excludes data 632. For example, in these implementations, the trained model 634 may be generated, e.g., on a different device, and be provided as part of machine-learning application 630. In various implementations, the trained model 634 may be provided as a data file that includes a model structure or form, and associated weights. Inference engine 636 may read the data file for trained model 634 and implement a neural network with node connectivity, layers, and weights based on the model structure or form specified in trained model 634.

Machine-learning application 630 also includes a trained model 634. In some implementations, the trained model may include one or more model forms or structures. For example, model forms or structures can include any type of neural-network, such as a linear network, a deep neural network that implements a plurality of layers (e.g., "hidden layers" between an input layer and an output layer, with each layer being a linear network), a convolutional neural network (e.g., a network that splits or partitions input data into multiple parts or tiles, processes each tile separately using one or more neural-network layers, and aggregates the results from the processing of each tile), a sequence-to-sequence neural network (e.g., a network that takes as input sequential data, such as words in a sentence, frames in a video, etc. and produces as output a result sequence), etc. The model form or structure may specify connectivity between various nodes and organization of nodes into layers. For example, nodes of a first layer (e.g., input layer) may receive data as input data 632 or application data 614. Such data can include, for example, one or more pixels per node, e.g., when the trained model is used for image analysis. Subsequent intermediate layers may receive as input output of nodes of a previous layer per the connectivity specified in the model form or structure. These layers may also be referred to as hidden layers. A final layer (e.g., output layer) produces an output of the machine-learning application. For example, the output may be a set of labels for an image, a representation of the image that permits comparison of the image to other images (e.g., a feature vector for the image), an output sentence in response to an input sentence, one or more categories for the input data, etc. depending on the specific trained model. In some implementations, model form or structure also specifies a number and/or type of nodes in each layer.

In different implementations, trained model 634 can include a plurality of nodes, arranged into layers per the model structure or form. In some implementations, the nodes may be computational nodes with no memory, e.g., configured to process one unit of input to produce one unit of output. Computation performed by a node may include, for example, multiplying each of a plurality of node inputs by a weight, obtaining a weighted sum, and adjusting the weighted sum with a bias or intercept value to produce the node output. In some implementations, the computation performed by a node may also include applying a step/activation function to the adjusted weighted sum. In some implementations, the step/activation function may be a non-linear function. In various implementations, such computation may include operations such as matrix multiplication. In some implementations, computations by the plurality of nodes may be performed in parallel, e.g., using multiple processors cores of a multicore processor, using individual processing units of a GPU, or special-purpose neural circuitry. In some implementations, nodes may include memory, e.g., may be able to store and use one or more earlier inputs in processing a subsequent input. For example, nodes with memory may include long short-term memory (LSTM) nodes. LSTM nodes may use the memory to maintain "state" that permits the node to act like a finite state machine (FSM). Models with such nodes may be useful in processing sequential data, e.g., words in a sentence or a paragraph, frames in a video, speech or other audio, etc.

In some implementations, trained model 634 may include embeddings or weights for individual nodes. For example, a model may be initiated as a plurality of nodes organized into layers as specified by the model form or structure. At initialization, a respective weight may be applied to a connection between each pair of nodes that are connected per the model form, e.g., nodes in successive layers of the neural network. For example, the respective weights may be randomly assigned, or initialized to default values. The model may then be trained, e.g., using data 632, to produce a result.

For example, training may include applying supervised learning techniques. In supervised learning, the training data can include a plurality of inputs (e.g., a set of images) and a corresponding expected output for each input (e.g., one or more labels for each image). Based on a comparison of the output of the model with the expected output, values of the weights are automatically adjusted, e.g., in a manner that increases a probability that the model produces the expected output when provided similar input.

In some implementations, training may include applying unsupervised learning techniques. In unsupervised learning, only input data may be provided and the model may be trained to differentiate data, e.g., to cluster input data into a plurality of groups, where each group includes input data that are similar in some manner. For example, the model may be trained to differentiate images such that the model distinguishes abstract images (e.g., synthetic images, human-drawn images, etc.) from natural images (e.g., photos). The model may be trained to determine one or more image characteristics based on image content data and/or image metadata. The determined image characteristics may include image labels and/or semantic concepts.

In another example, a model trained using unsupervised learning may cluster words based on the use of the words in input sentences. In some implementations, unsupervised learning may be used to produce knowledge representations, e.g., that may be used by machine-learning application 630. In various implementations, a trained model includes a set of weights, or embeddings, corresponding to the model structure. In implementations where data 632 is omitted, machine-learning application 630 may include trained model 634 that is based on prior training, e.g., by a developer of the machine-learning application 630, by a third-party, etc. In some implementations, trained model 634 may include a set of weights that are fixed, e.g., downloaded from a server that provides the weights.

Machine-learning application 630 also includes an inference engine 636. Inference engine 636 is configured to apply the trained model 634 to data, such as application data 614, to provide an inference. In some implementations, inference engine 636 may include software code to be executed by processor 602. In some implementations, inference engine 636 may specify circuit configuration (e.g., for a programmable processor, for a field programmable gate array (FPGA), etc.) enabling processor 602 to apply the trained model. In some implementations, inference engine 636 may include software instructions, hardware instructions, or a combination. In some implementations, inference engine 636 may offer an application programming interface (API) that can be used by operating system 608 and/or other applications 612 to invoke inference engine 636, e.g., to apply trained model 634 to application data 614 to generate an inference.

Machine-learning application 630 may provide several technical advantages. For example, when trained model 634 is generated based on unsupervised learning, trained model 634 can be applied by inference engine 636 to produce knowledge representations (e.g., numeric representations) from input data, e.g., application data 614. For example, a model trained for image analysis may produce representations of images that have a smaller data size (e.g., 1 KB) than input images (e.g., 10 MB). In some implementations, such representations may be helpful to reduce processing cost (e.g., computational cost, memory usage, etc.) to generate an output (e.g., a label, a classification, a sentence descriptive of the image, etc.). In some implementations, such representations may be provided as input to a different machine-learning application that produces output from the output of inference engine 636. In some implementations, knowledge representations generated by machine-learning application 630 may be provided to a different device that conducts further processing, e.g., over a network. In such implementations, providing the knowledge representations rather than the images may provide a technical benefit, e.g., enable faster data transmission with reduced cost. In another example, a model trained for clustering documents may produce document clusters from input documents. The document clusters may be suitable for further processing (e.g., determining whether a document is related to a topic, determining a classification category for the document, etc.) without the need to access the original document, and therefore, save computational cost.

In some implementations, machine-learning application 630 may be implemented in an offline manner. In these implementations, trained model 634 may be generated in a first stage, and provided as part of machine-learning application 630. In some implementations, machine-learning application 630 may be implemented in an online manner. For example, in such implementations, an application that invokes machine-learning application 630 (e.g., operating system 608, one or more of other applications 612) may utilize an inference produced by machine-learning application 630, e.g., provide the inference to a user, and may generate system logs (e.g., if permitted by the user, an action taken by the user based on the inference; or if utilized as input for further processing, a result of the further processing). System logs may be produced periodically, e.g., hourly, monthly, quarterly, etc. and may be used, with user permission, to update trained model 634, e.g., to update embeddings for trained model 634.

In some implementations, machine-learning application 630 may be implemented in a manner that can adapt to particular configuration of device 600 on which the machine-learning application 630 is executed. For example, machine-learning application 630 may determine a computational graph that utilizes available computational resources, e.g., processor 602. For example, if machine-learning application 630 is implemented as a distributed application on multiple devices, machine-learning application 630 may determine computations to be carried out on individual devices in a manner that optimizes computation. In another example, machine-learning application 630 may determine that processor 602 includes a GPU with a particular number of GPU cores (e.g., 1000) and implement the inference engine accordingly (e.g., as 1000 individual processes or threads).

In some implementations, machine-learning application 630 may implement an ensemble of trained models. For example, trained model 634 may include a plurality of trained models that are each applicable to same input data. In these implementations, machine-learning application 630 may choose a particular trained model, e.g., based on available computational resources, success rate with prior inferences, etc. In some implementations, machine-learning application 630 may execute inference engine 636 such that a plurality of trained models is applied. In these implementations, machine-learning application 630 may combine outputs from applying individual models, e.g., using a voting-technique that scores individual outputs from applying each trained model, or by choosing one or more particular outputs. Further, in these implementations, machine-learning application may apply a time threshold for applying individual trained models (e.g., 0.5 ms) and utilize only those individual outputs that are available within the time threshold. Outputs that are not received within the time threshold may not be utilized, e.g., discarded. For example, such approaches may be suitable when there is a time limit specified while invoking the machine-learning application, e.g., by operating system 608 or one or more applications 612.

In different implementations, machine-learning application 630 can produce different types of outputs. For example, machine-learning application 630 can provide representations or clusters (e.g., numeric representations of input data), labels (e.g., for input data that includes images, documents, etc.), phrases or sentences (e.g., descriptive of an image or video, suitable for use as a response to an input sentence, etc.), images (e.g., generated by the machine-learning application in response to input), audio or video (e.g., in response an input video, machine-learning application 630 may produce an output video with a particular effect applied, e.g., rendered in a comic-book or particular artist's style, when trained model 634 is trained using training data from the comic book or particular artist, etc. In some implementations, machine-learning application 630 may produce an output based on a format specified by an invoking application, e.g. operating system 608 or one or more applications 612. In some implementations, an invoking application may be another machine-learning application. For example, such configurations may be used in generative adversarial networks, where an invoking machine-learning application is trained using output from machine-learning application 630 and vice-versa.

Any of software in memory 604 can alternatively be stored on any other suitable storage location or computer-readable medium. In addition, memory 604 (and/or other connected storage device(s)) can store one or more images, messages, one or more taxonomies, electronic encyclopedia, dictionaries, thesauruses, knowledge bases, message data, grammars, user preferences, and/or other instructions and data used in the features described herein. Memory 604 and any other type of storage (magnetic disk, optical disk, magnetic tape, or other tangible media) can be considered "storage" or "storage devices."

I/O interface 606 can provide functions to enable interfacing the server device 600 with other systems and devices. Interfaced devices can be included as part of the device 600 or can be separate and communicate with the device 600. For example, network communication devices, storage devices (e.g., memory and/or database 106), and input/output devices can communicate via I/O interface 606. In some implementations, the I/O interface can connect to interface devices such as input devices (keyboard, pointing device, touchscreen, microphone, camera, scanner, sensors, etc.) and/or output devices (display devices, speaker devices, printers, motors, etc.).

Some examples of interfaced devices that can connect to I/O interface 606 can include one or more display devices 620 that can be used to display content, e.g., images, video, and/or a user interface of an output application as described herein. Display device 620 can be connected to device 600 via local connections (e.g., display bus) and/or via networked connections and can be any suitable display device. Display device 620 can include any suitable display device such as an LCD, LED, or plasma display screen, CRT, television, monitor, touchscreen, 3-D display screen, or other visual display device. For example, display device 620 can be a flat display screen provided on a mobile device, multiple display screens provided in a goggles or headset device, or a monitor screen for a computer device.

The I/O interface 606 can interface to other input and output devices. Some examples include one or more cameras which can capture images. Some implementations can provide a microphone for capturing sound (e.g., as a part of captured images, voice commands, etc.), audio speaker devices for outputting sound, or other input and output devices.

For ease of illustration, FIG. 6 shows one block for each of processor 602, memory 604, I/O interface 606, and software blocks 608, 612, and 630. These blocks may represent one or more processors or processing circuitries, operating systems, memories, I/O interfaces, applications, and/or software modules. In other implementations, device 600 may not have all of the components shown and/or may have other elements including other types of elements instead of, or in addition to, those shown herein. While some components are described as performing blocks and operations as described in some implementations herein, any suitable component or combination of components of environment 100, device 600, similar systems, or any suitable processor or processors associated with such a system, may perform the blocks and operations described.

Methods described herein can be implemented by computer program instructions or code, which can be executed on a computer. For example, the code can be implemented by one or more digital processors (e.g., microprocessors or other processing circuitry) and can be stored on a computer program product including a non-transitory computer readable medium (e.g., storage medium), such as a magnetic, optical, electromagnetic, or semiconductor storage medium, including semiconductor or solid state memory, magnetic tape, a removable computer diskette, a random access memory (RAM), a read-only memory (ROM), flash memory, a rigid magnetic disk, an optical disk, a solid-state memory drive, etc. The program instructions can also be contained in, and provided as, an electronic signal, for example in the form of software as a service (SaaS) delivered from a server (e.g., a distributed system and/or a cloud computing system). Alternatively, one or more methods can be implemented in hardware (logic gates, etc.), or in a combination of hardware and software. Example hardware can be programmable processors (e.g. Field-Programmable Gate Array (FPGA), Complex Programmable Logic Device), general purpose processors, graphics processors, Application Specific Integrated Circuits (ASICs), and the like. One or more methods can be performed as part of or component of an application running on the system, or as an application or software running in conjunction with other applications and operating system.

Although the description has been described with respect to particular implementations thereof, these particular implementations are merely illustrative, and not restrictive. Concepts illustrated in the examples may be applied to other examples and implementations.

Note that the functional blocks, operations, features, methods, devices, and systems described in the present disclosure may be integrated or divided into different combinations of systems, devices, and functional blocks as would be known to those skilled in the art. Any suitable programming language and programming techniques may be used to implement the routines of particular implementations. Different programming techniques may be employed, e.g., procedural or object-oriented. The routines may execute on a single processing device or multiple processors. Although the steps, operations, or computations may be presented in a specific order, the order may be changed in different particular implementations. In some implementations, multiple steps or operations shown as sequential in this specification may be performed at the same time.

What is claimed is:

1. A method comprising:
   receiving first user input indicative of selection of one or more first images in an image library;
   determining one or more first image characteristics of the one or more first images;
   identifying one or more second images in the image library, wherein each of the one or more second images is associated with at least one second image characteristic that matches at least one of the one or more first image characteristics;
   causing a user interface to be displayed, wherein the user interface includes the one or more second images, wherein the user interface enables selection of the one or more second images, and wherein causing the user interface to be displayed includes causing the one or more second images to be displayed in a particular section of the user interface;
   receiving second user input indicative of selection of at least one particular second image of the one or more second images;
   in response to receiving the second user input, determining one or more second image characteristics of the at least one particular second image;
   identifying one or more third images in the image library, wherein each of the one or more third images is associated with at least one third image characteristic that matches at least one of the one or more first image characteristics and at least one of the one or more second image characteristics;
   causing an updated user interface to be displayed, wherein the updated user interface includes the one or more third images, wherein the updated user interface enables selection of the one or more third images, and wherein causing the updated user interface to be displayed includes updating the particular section of the user interface to display at least one of the one or more third images in place of at least one of the one or more second images; and
   displaying, in the updated user interface, one or more recent images that were captured or received within a particular time period prior to a current time, wherein the particular section of the user interface is displayed overlaying at least a portion of the recent images.

2. The method of claim 1, further comprising generating an image album, wherein the image album includes the one or more first images and the at least one of the one or more second images.

3. The method of claim 1, further comprising:
   generating an image collage, wherein the image collage includes the one or more first images and the at least one particular second image.

4. The method of claim 1, wherein determining the one or more first image characteristics comprises determining that at least one of the one or more first images is blurry, and wherein identifying the one or more second images includes identifying each of the one or more second images based on blurriness of the one or more second images.

5. The method of claim 1, wherein determining the one or more first image characteristics comprises determining a location associated with at least one of the one or more first images, and wherein identifying the one or more second images comprises selecting images from the image library that are associated with a respective location that is within a threshold distance of the location associated with the at least one of the one or more first images.

6. The method of claim 1, further comprising determining a context of image selection, wherein identifying the one or more second images is based on the context of image selection, wherein the context of image selection is one of generation of an image-based creation or providing images to a target software application, and wherein the image-based creation comprises at least one of an image album, an image collage, a video, or a printed publication.

7. The method of claim 1, wherein
   displaying, in the updated user interface, one or more recent images that were captured or received within a particular time period prior to a current time, wherein
   the one or more first images and the at least one particular second image are displayed in a tray section of the user interface that is distinct from the displayed one or more recent images.

8. The method of claim 1, wherein the one or more second images are a plurality of second images,
   wherein causing the one or more second images to be displayed in the particular section of the user interface includes causing a first group of the plurality of second images to be displayed in a first portion of the particular section and a second group of the plurality of second images to be displayed in a second portion of the particular section,
   wherein the first group has a greater degree of match with the one or more first images than the second group.

9. The method of claim 1, further comprising:
   based on the one or more first images and the at least one of the one or more second images, causing a suggested action element to be displayed in the user interface.

10. The method of claim 9, further comprising:
    receiving user selection of the suggested action element; and
    in response to receiving the user selection, performing an action associated with the suggested action element, wherein the action includes one or more of archiving the one or more first images and the at least one of the one or more second images, deleting the one or more first images and the at least one of the one or more second images, or performing an automatic enhancement of the one or more first images and the at least one of the one or more second images.

11. A method comprising:
- determining context information indicative of a target software application, wherein the context information includes one or more images received from the target software application;
- identifying one or more first images in an image library based at least in part on matching the context information with image characteristics of the one or more first images;
- causing a user interface to be displayed, wherein the user interface includes the one or more first images, and wherein the user interface enables selection of the one or more first images;
- receiving first user input indicative of selection of at least one first image of the one or more first images;
- in response to receiving the first user input, determining one or more first image characteristics of the at least one first image and providing the at least one first image to the target software application;
- identifying one or more second images in the image library, wherein each of the one or more second images is associated with at least one second image characteristic that matches at least one of the one or more first image characteristics;
- causing the one or more second images to be displayed in a particular section of the user interface, wherein the user interface enables selection of the one or more second images;
- receiving second user input indicative of selection of at least one particular second image of the one or more second images;
- in response to receiving the second user input, determining one or more second image characteristics of the at least one particular second image;
- identifying one or more third images in the image library, wherein each of the one or more third images is associated with at least one third image characteristic that matches at least one of the one or more first image characteristics and at least one of the one or more second image characteristics;
- causing an updated user interface to be displayed, wherein the updated user interface includes the one or more third images, wherein the updated user interface enables selection of the one or more third images, and wherein causing the updated user interface to be displayed includes updating the particular section of the user interface to display at least one of the one or more third images in place of at least one of the one or more second images; and
- displaying, in the updated user interface, one or more recent images that were captured or received within a particular time period prior to a current time, wherein the particular section of the user interface is displayed overlaying at least a portion of the recent images.

12. The method of claim 11, further comprising:
- based on the one or more first images and the at least one of the one or more second images, causing a suggested action element to be displayed in the user interface;
- receiving user selection of the suggested action element; and
- in response to receiving the user selection, performing an action associated with the suggested action element, wherein the action includes one or more of archiving the one or more first images and the at least one of the one or more second images, deleting the one or more first images and the at least one of the one or more second images, or performing an automatic enhancement of the one or more first images and the at least one of the one or more second images.

13. The method of claim 11, wherein determining the context information includes determining an application type of the target software application.

14. The method of claim 13, wherein the application type includes an image sharing application, and wherein identifying the one or more first images comprises:
- selecting the one or more first images from the image library that meet a quality threshold.

15. The method of claim 13, wherein the application type includes a financial application, and wherein identifying the one or more first images comprises:
- selecting the one or more first images from the image library, wherein the one or more first images are associated with an image label that includes one or more of receipt, document, or screenshot.

16. The method of claim 13, wherein the application type includes a messaging application, and wherein determining the context information further includes receiving identification information of participants in a messaging conversation in the messaging application, and wherein identifying the one or more first images comprises:
- selecting images from the image library that depict at least one of the participants in the messaging conversation.

17. The method of claim 11, wherein determining the context information comprises receiving an application context from the target software application, and wherein identifying the one or more first images comprises:
- determining one or more semantic concepts based on the application context; and
- selecting the one or more first images, wherein at least one image characteristic of each of the one or more first images matches at least one of the one or more semantic concepts.

18. A non-transitory computer-readable medium with instructions stored thereon that, when executed by one or more hardware processors, cause the one or more hardware processors to perform operations comprising:
- receiving first user input indicative of selection of one or more first images in an image library;
- determining one or more first image characteristics of the one or more first images;
- identifying one or more second images in the image library, wherein each of the one or more second images is associated with at least one second image characteristic that matches at least one of the one or more first image characteristics;
- causing a user interface to be displayed, wherein the user interface includes the one or more second images, wherein the user interface enables selection of the one or more second images, and wherein causing the user interface to be displayed includes causing the one or more second images to be displayed in a particular section of the user interface;
- receiving second user input indicative of selection of at least one second image of the one or more second images;
- in response to receiving the second user input, determining one or more second image characteristics of the at least one second image;
- identifying one or more third images in the image library, wherein each of the one or more third images is associated with at least one third image characteristic that matches at least one of the one or more first image characteristics and at least one of the one or more second image characteristics;

causing an updated user interface to be displayed, wherein the updated user interface includes the one or more third images, wherein the updated user interface enables selection of the one or more third images, and wherein causing the updated user interface to be displayed includes updating the particular section of the user interface to display at least one of the one or more third images in place of at least one of the one or more second images;

displaying, in the updated user interface, one or more recent images that were captured or received within a particular time period prior to a current time, wherein the particular section of the user interface is displayed overlaying at least a portion of the recent images;

based on the one or more first images and the at least one of the one or more second images, causing a suggested action element to be displayed in the user interface; and in response to receiving user selection of the suggested action element, performing an action associated with the suggested action element, wherein the action includes one or more of archiving the one or more first images and the at least one of the one or more second images, deleting the one or more first images and the at least one of the one or more second images, or performing an automatic enhancement of the one or more first images and the at least one of the one or more second images.

* * * * *